(12) United States Patent
Jenkins

(10) Patent No.: US 8,163,701 B2
(45) Date of Patent: Apr. 24, 2012

(54) PRODRUGS OF ACTIVE AGENTS

(75) Inventor: Thomas E. Jenkins, La Honda, CA (US)

(73) Assignee: Signature Therapeutics, Inc., San Carlos, CA (US)

(*) Notice: Subject to any disclaimer, the term of this patent is extended or adjusted under 35 U.S.C. 154(b) by 1415 days.

(21) Appl. No.: 11/508,042

(22) Filed: Aug. 21, 2006

(65) Prior Publication Data

US 2007/0123468 A1 May 31, 2007

Related U.S. Application Data

(60) Provisional application No. 60/711,438, filed on Aug. 19, 2005, provisional application No. 60/711,862, filed on Aug. 25, 2005, provisional application No. 60/760,762, filed on Jan. 20, 2006, provisional application No. 60/799,532, filed on May 10, 2006.

(51) Int. Cl.
  A61K 38/00 (2006.01)
  A61K 51/00 (2006.01)
  A61K 31/785 (2006.01)
  A61P 25/04 (2006.01)
  C07K 2/00 (2006.01)
  C07K 4/00 (2006.01)
  C07K 5/00 (2006.01)
  C07K 7/00 (2006.01)
  C07K 14/00 (2006.01)
  C07K 16/00 (2006.01)
  C07K 17/00 (2006.01)

(52) U.S. Cl. ...................... 514/18.4; 514/1.1; 424/78.16; 424/1.69; 436/901; 530/300

(58) Field of Classification Search .................. None
See application file for complete search history.

(56) References Cited

U.S. PATENT DOCUMENTS

2005/0182258 A1 8/2005 Schmidhammer et al.

FOREIGN PATENT DOCUMENTS

| DE | 43 08 095 | | 9/1994 |
|---|---|---|---|
| EP | 0 170 090 | | 2/1986 |
| EP | 0 615 756 | | 9/1994 |
| WO | WO 2004/005294 | * | 1/2004 |
| WO | WO 2004/039317 | | 5/2004 |

OTHER PUBLICATIONS

Vippagunta et al. Crystalline Solids. Adv. Drug Delivery Rev. 48 (2001), 3-26.*
Kudryashova et al. (Khimiko-Farmatsevticheskii Zhurnal (1973), 7(8), 5-6) (abstract included, available upon request from Applicant if needed still; relevance is 3 compounds/RN numbers thereof).*
International Search Report for International Application No. PCT/US2006/032734, mailed Feb. 2, 2007.
de Groot et al., *J. Med. Chem.*, 43, 3093-3102 (2000).
de Groot et al., *J. Org. Chem.*, 66, 8815-8830 (2001).
Papot et al., *Curr. Med. Chem.—Anti-Cancer Agents*, 2, 155-185 (2002).
Portoghese et al., *J. Med. Chem.*, 37, 579-585 (1994).
Schmidhammer et al., *J. Med. Chem.*, 27, 1575-1579 (1984).
Toki et al., *J. Org. Chem.*, 67, 1866-1872 (2002).
Wermuth et al., "Designing Prodrugs and Bioprecursors I: Carrier Prodrugs", in The Practice of Medicinal Chemistry, 671-696 (1996).

* cited by examiner

*Primary Examiner* — Maury Audet
(74) *Attorney, Agent, or Firm* — Connie C. Tong; Carol L. Francis; Bozicevic, Field & Francis LLP

(57) ABSTRACT

Disclosed herein are prodrugs of active agents which contain at least one amine, phenol, carboxylic acid, or thiol functionality. Also disclosed herein are methods of making prodrugs of active agents, pharmaceutical compositions of prodrugs of active agents and methods of using prodrugs of active agents and pharmaceutical compositions.

28 Claims, 1 Drawing Sheet

PRODRUGS OF ACTIVE AGENTS

Figure 1A:
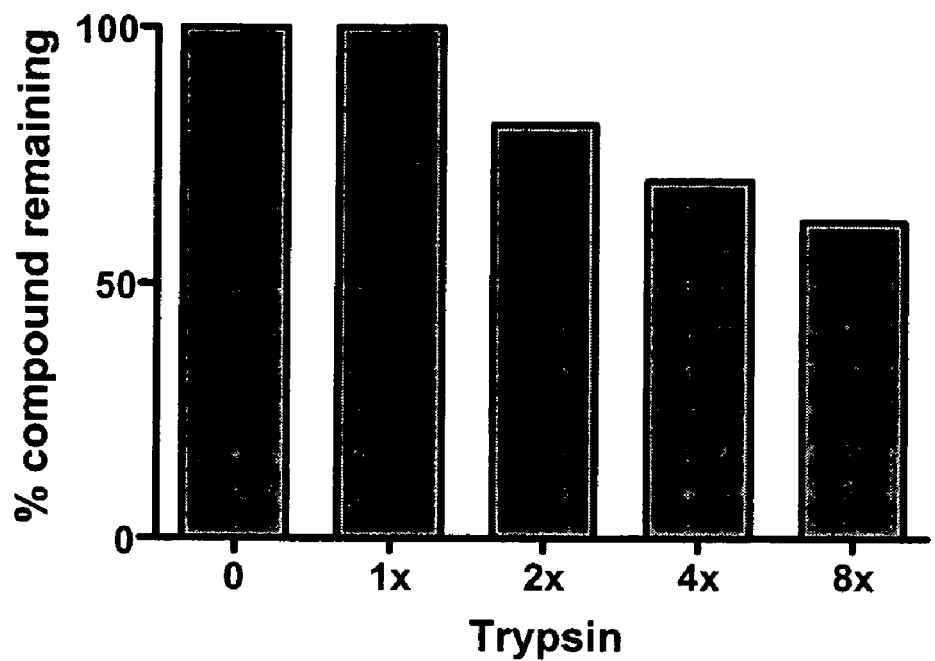

This application claims the benefit under 35 U.S.C. §19(e) from U. S. Provisional Application Ser. Nos. 60/711,438, 60/711,862, 60/760,762 and 60/799,532 filed on Aug. 19, 2005, Aug. 25, 2005, Jan. 20, 2006 and May 10, 2006, respectively, which are herein incorporated by reference in their entirety.

1. TECHNICAL FIELD

Disclosed herein are prodrugs of active agents which contain at least one amine, phenol, carboxylic acid or thiol functionality. Also disclosed herein are methods of making prodrugs of active agents, pharmaceutical compositions of prodrugs of active agents and methods of using prodrugs of active agents and pharmaceutical compositions thereof.

2. BACKGROUND

Delivery systems are often essential in safely administering active agents. Delivery systems can be used to optimize bioavailability, improve dosage consistency and improve patient compliance (e.g., by reducing dosing frequency). Solutions to drug delivery and/or bioavailability issues in pharmaceutical development include, for example, converting known active agents to prodrugs. Typically, in a prodrug, a polar functional group (e.g., a carboxylic acid, an amino group, phenol group, a sulfhydryl group, etc.) of the active agent is masked by a promoiety, which is labile under physiological conditions. Accordingly, prodrugs are usually transported through hydrophobic biological barriers such as membranes and may possess superior physicochemical properties in comparison to the parent drug. Prodrugs are preferably non-toxic and are preferably selectively cleaved at the locus of drug action. Ideally, cleavage of the promoiety occurs rapidly and quantitatively with the formation of non-toxic by-products (i.e., the hydrolyzed promoiety).

Many active agents, particularly those that are orally available, are susceptible to intentional abuse (e.g., narcotics, amphetamines and other controlled substances) or unintentional abuse (e.g., overdose by impaired or non-compliant patients or infants). Conventional methods such as microencapsulation and enteric coating technologies, although successful in delivering many active agents, have had limited success in reducing abuse of active agents such as narcotics, amphetamines, etc.

Accordingly what is needed are prodrugs of active agents, which in addition to potentially increasing bioavailability and having superior physiochemical properties, are also resistant to patient abuse.

3. SUMMARY

Disclosed herein are prodrugs of active agents, pharmaceutical compositions thereof and methods of using these prodrugs and pharmaceutical compositions thereof which satisfy the above needs. In some embodiments, the prodrugs of active agents may be orally administered.

Generally, an active agent contains at least one amine, phenol, carboxylic acid, or thiol functionality, which can be functionalized with a promoiety. The promoiety of the prodrug includes a spacer group and a cleavable moiety where the spacer group may electronically decouple and/or sterically separate the active agent from the cleavable moiety. Accordingly, a prodrug disclosed herein generally comprises an active agent attached through a heteroatom to a spacer group which is further attached to a cleavable moiety. In some embodiments, the cleavable moiety is cleaved enzymatically. In other embodiments, the cleavable moiety is cleaved by hydrolysis.

In some embodiments, a compound of structural Formula (I) is provided:

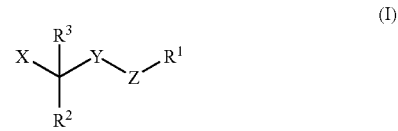

(I)

or salts, solvates or hydrates thereof wherein:

X is an active agent comprising an amine, phenol, carboxylic acid or thiol wherein a hydrogen atom of the primary or secondary amine, phenol, carboxylic acid or thiol is replaced by a covalent bond to $-(CR^2R^3)-Y-Z-R^1$ or a lone pair of a tertiary amine is replaced by a covalent bond to $-(CR^2R^3)-Y-Z-R^1$;

$R^2$ and $R^3$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Y is aryl, heteroaryl or arylaryl optionally substituted with one or more $-F$, $-Cl$, $-Br$, $-I$, $-R^4$, $-O^-$, $-OR^4$, $-SR^4$, $-S^-$, $-NR^4R^5$, $-CF_3$, $-CN$, $-OCN$, $-SCN$, $-NO$, $-NO_2$, $-N_3$, $-S(O)_2O^-$, $-S(O)_2OH$, $-S(O)_2R^4$, $-OS(O_2)O^-$, $-OS(O)_2R^4$, $-P(O)(O^-)_2$, $-P(O)(OR^4)(O^-)$, $-OP(O)(OR^4)(OR^5)$, $-C(O)R^4$, $-C(S)R^4$, $-C(O)OR^4$, $-C(O)NR^4R^5$, $-C(O)O^-$, $-C(S)OR^4$, $-NR^6C(O)NR^4R^5$, $-NR^6C(S)NR^4R^5$, $-NR^7C(NR^6)NR^5R^4$ or $-C(NR^6)NR^5R^4$;

$R^4$, $R^5$, $R^6$ and $R^7$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^4$ and $R^5$ together with the nitrogen atom to which they are bonded form a cycloheteroalkyl or substituted cycloheteroalkyl ring;

Z is $-N(R^8)-$, $-O-$ or $-S-$;

$R^8$ is hydrogen, alkyl, substituted alkyl, aryl, substituted aryl, arylalkyl, substituted arylalkyl, heteroaryl, substituted heteroaryl, heteroarylalkyl, substituted heteroarylalkyl or

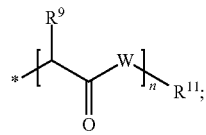

each W is independently $-NR^{10}-$, $-O-$ or $-S-$;

each $R^9$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^9$ and $R^{10}$ together with the atoms to which they are bonded form a cycloheteroalkyl or substituted cycloheteroalkyl ring;

each $R^{10}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{10}$ and $R^{11}$ together with the atoms to which they are bonded form a cycloheteroalkyl or substituted cycloheteroalkyl ring;

$R^{11}$ is hydrogen, alkyl, substituted alkyl, aryl, substituted aryl, arylalkyl or substituted arylalkyl;

n is an integer from 0 to 5; or n is an integer from 1 to 5;
$R^1$ is

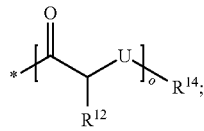

each U is independently —$NR^{13}$—, —O— or —S—;

each $R^{12}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{12}$ and $R^{13}$ together with the atoms to which they are bonded form a cycloheteroalkyl or substituted cycloheteroalkyl ring;

each $R^{13}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{13}$ and $R^{14}$ together with the atoms to which they are bonded form a cycloheteroalkyl or substituted cycloheteroalkyl ring;

$R^{14}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 5; and provided that Z is oriented para or ortho to X—($CR^2R^3$).

In other embodiments of a compound of structural Formula (I), X is an opioid;

$R^2$ and $R^3$ are independently hydrogen, alkyl, aryl or arylalkyl;

Y is phenyl, naphthyl, anthracenyl or biphenyl, optionally substituted with one or more —F, —Cl, —Br, —I, —$R^3$, —$OR^3$, —$SR^3$, —$NR^3R^4$, —$CF_3$, —CN, —$NO_2$, —$N_3$, —$S(O)_2O^-$, —$S(O)_2OH$, —$S(O)_2R^3$, —$P(O)(O^-)_2$, —$P(O)(OR^2)(O^-)$, —$OP(O)(OR^3)(OR^3)$, —$C(O)R^3$, —$C(O)OR^3$, —$C(O)NR^3R^4$, or —$C(O)O^-$, Z is —$N(R^8)$—;

$R^{10}$ is hydrogen, alkyl, aryl or arylalkyl;

each $R^9$ is independently, hydrogen, alkanyl, substituted alkanyl, aryl, arylalkanyl, cycloalkanyl, substituted cycloalkanyl, substituted arylalkanyl or heteroarylalkanyl or optionally, each $R^9$ and $R^{10}$ independently, together with the atoms to which they are attached form a cycloheteroalkanyl or substituted cycloheteroalkanyl ring;

$R^{13}$ is hydrogen, alkyl, aryl or arylalkyl; and each $R^{12}$ is independently, hydrogen, alkanyl, substituted alkanyl, aryl, arylalkanyl, cycloalkanyl, substituted cycloalkanyl, substituted arylalkanyl or heteroarylalkanyl or optionally, each $R^{12}$ and $R^{13}$ independently, together with the atoms to which they are attached form a cycloheteroalkanyl or substituted cycloheteroalkanyl ring.

In still other embodiments of a compound of structural Formula (I), X is an opioid;

$R^2$ and $R^3$ are independently hydrogen, alkyl, aryl or arylalkyl;

Y is phenyl, naphthyl, anthracenyl or biphenyl, optionally substituted with one or more —F, —Cl, —Br, —I, —$R^3$, —$OR^3$, —$SR^3$, —$NR^3R^4$, —$CF_3$, —CN, —$NO_2$, —$N_3$, —$S(O)_2O^-$, —$S(O)_2OH$, —$S(O)_2R^3$, —$P(O)(O^-)_2$, —$P(O)(OR^2)(O^-)$, —$OP(O)(OR^3)(OR^3)$, —$C(O)R^3$, —$C(O)OR^3$, —$C(O)NR^3R^4$, or —$C(O)O^-$, Z is —$N(R^8)$—;

$R^{10}$ is hydrogen, alkyl, aryl or arylalkyl;

each $R^9$ is independently, hydrogen, alkanyl, substituted alkanyl, aryl, arylalkanyl, cycloalkanyl, substituted cycloalkanyl, substituted arylalkanyl or heteroarylalkanyl or optionally, each $R^9$ and $R^{10}$ independently, together with the atoms to which they are attached form a cycloheteroalkanyl or substituted cycloheteroalkanyl ring;

$R^{13}$ is hydrogen, alkyl, aryl or arylalkyl; and each $R^{12}$ is independently, hydrogen, alkanyl, substituted alkanyl, aryl, arylalkanyl, cycloalkanyl, substituted cycloalkanyl, substituted arylalkanyl or heteroarylalkanyl or optionally, each $R^{12}$ and $R^{13}$ independently, together with the atoms to which they are attached form a cycloheteroalkanyl or substituted cycloheteroalkanyl ring.

In another aspect, pharmaceutical compositions are provided which generally comprise one or more compounds of Formula (I), salts, hydrates, solvates or N-oxides thereof and a pharmaceutically acceptable vehicle such as a diluent, carrier, excipient or adjuvant. The choice of diluent, carrier, excipient and adjuvant will depend upon, among other factors, the desired mode of administration.

In still another aspect, methods for treating or deterring various diseases or disorders are provided. The methods generally involve administering to a patient in need of such treatment or prevention a therapeutically effective amount of a compound Formula (I) and/or a pharmaceutical composition thereof.

In still another aspect, methods of deterring abuse of opioids is provided. The methods generally involve administering to a patient in need of such prevention a therapeutically effective amount of a compound Formula (I) and/or a pharmaceutical composition thereof.

In still another aspect, methods of deterring abuse of amphetamines is provided. The methods generally involve administering to a patient in need of such prevention a therapeutically effective amount of a compound Formula (I) and/or a pharmaceutical composition thereof.

BRIEF DESCRIPTIONS OF THE DRAWINGS

Figure 1B:
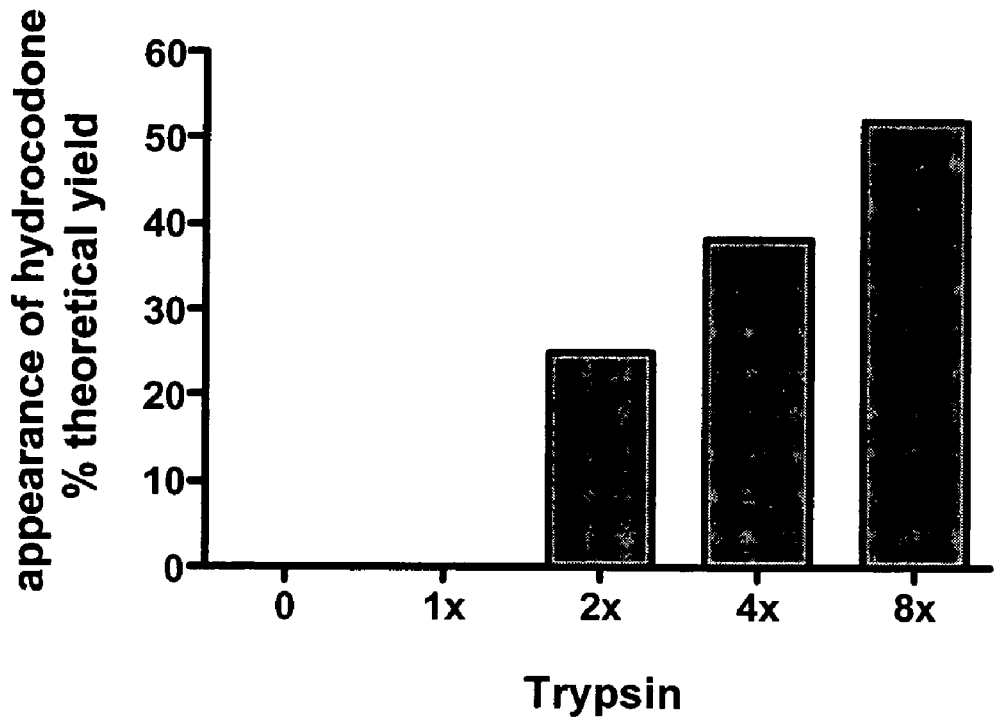

FIGS. 1A-B show the hydrolysis of the opioid prodrug Z with trypsin (FIG. 1A) and the appearance of hydrocodone (FIG. 1B).

4. DETAILED DESCRIPTION 4.1 Definitions

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds 20 and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cyclohexylcarbonyl, cyclohexylmethylcarbonyl, benzoyl, benzylcarbonyl and the like.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)OR$^{31}$ where R$^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms. In other embodiments, an aryl group comprises from 6 to 12 carbon atoms.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophylethan-1-yl and the like. Where specific alkyl moieties are intended, the nomenclature arylalkanyl, arylalkenyl and/or arylalkynyl is used. In some embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In other embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group are specified, the numbers refer to the carbon atoms comprising each parent aromatic ring. For example, ($C_5$-$C_{14}$) arylaryl is an arylaryl group in which each aromatic ring comprises from 5 to 14 carbons, e.g., biphenyl, triphenyl, binaphthyl, phenylnapthyl, etc. In some embodiments, each parent aromatic ring system of an arylaryl group is independently a ($C_5$-$C_{14}$) aromatic. In other embodiments, each parent aromatic ring system of an arylaryl group is independently a ($C_5$-$C_{10}$) aromatic. In still other embodiments, each parent aromatic ring system is identical, e.g., biphenyl, triphenyl, binaphthyl, trinaphthyl, etc.

"Compounds" as used herein refers to compounds encompassed by structural Formula (I) disclosed herein and includes any specific compounds within this formula whose structure is disclosed herein. Compounds may be identified either by their chemical structure and/or chemical name. The compounds described herein may contain one or more chiral centers and/or double bonds and therefore, may exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present disclosure.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In some embodiments, the cycloalkyl group is ($C_3$-$C_{10}$) cycloalkyl. In other embodiments, the cycloalkyl group is ($C_3$-$C_7$) cycloalkyl.

"Cycloheteroalkyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$—, —SO—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is from 5-20 membered heteroaryl. In other embodiments, the heteroaryl group is from 5-10 membered heteroaryl. In still other embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In some embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In other embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Parent Aromatic Ring System" by itself or as part of another substituent, refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" by itself or as part of another substituent, refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutical composition" refers to at least one compound and a pharmaceutically acceptable vehicle, with which the compound is administered to a patient.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound is administered.

"Patient" includes mammal humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a active agent that requires a transformation within the body to release the active agent. In some embodiments, the transformation is an enzymatic transformation. Prodrugs are frequently, although not necessarily, pharmacologically inactive until converted to the active agent.

"Promoiety" refers to a form of protecting group that when used to mask a functional group within an active agent converts the active agent into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry," (Wiley, $2^{nd}$ ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are independently replaced with the same or different substituent(s). Typical substituents include, but are not limited to, -M, $-R^{60}$, $-O^-$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2O^-$, $-S(O)_2OH$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-NR^{62}C(S)NR^{60}R^{61}$, $-NR^{62}C(NR^{63})NR^{60}R^{61}$ and $-C(NR^{62})NR^{60}R^{61}$ where M is independently a halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and R64 and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. Preferably, substituents include -M, $-R^{60}$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2R^{60}$, $-OS(O_2)O^-$, $-OS(O)_2R^{60}$, $-P(O)(O^-)2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-NR^{62}C(O)NR^{60}R^{61}$, more preferably, -M, $-R^{60}$, $=O$, $-OR^{60}$, $-SR^{60}$, $-NR^{60}R^{61}$, $-CF_3$, $-CN$, $-NO_2$, $-S(O)_2R^{60}$, $-P(O)(OR^{60})(O^-)$, $-OP(O)(OR^{60})(OR^{61})$, $-C(O)R^{60}$, $-C(O)OR^{60}$, $-C(O)NR^{60}R^{61}$, $-C(O)O^-$, most preferably, -M, $-R^{60}$, $=O$, $-OR^{60}$, $-SR^{60}$, $-NR^{60}R^{61}$, $-CF_3$, $-CN$, $-NO_2$, $-S(O)_2R^{60}$, $-OP(O)(OR^{60})(OR^{61})$, $-C(O)R^{60}$, $-C(O)OR^{60}$, $-C(O)O^-$, where $R^{60}$, $R^{61}$ and $R^{62}$ are as defined above.

"Treating" or "treatment" of any disease or disorder refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter), or both. In still other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

Reference will now be made in detail to various embodiments. It will be understood that the invention is not limited to these embodiments. To the contrary, it is intended to cover alternatives, modifications, and equivalents as may be included within the spirit and scope of the allowed claims.

4.2 Prodrugs of Active Agents

Disclosed herein are prodrugs of active agents. Generally, the active agent contains at least one amine, phenol, carboxylic acid or thiol functionality, which can be functionalized with a promoiety. The promoiety includes a spacer group and a cleavable moiety where the spacer group may, inter alia, electronically decouple and/or physically separate the active agent from the cleavable moiety. Accordingly, a prodrug disclosed herein generally comprises an active agent attached through a heteroatom to a spacer which is further attached to a cleavable moiety.

Active agents include compounds with biological activity in treating or preventing various diseases. In some embodiments, active agents include drugs listed in references including, but not limited to, Physicians Desk Reference, $59^{th}$ Edition, and the Merck Index, $13^{th}$ Edition. In other embodiments, active agents include compounds with diagnostic utility. In still other embodiments, active agents comprise analgesics and other compounds for preventing, reducing, or delaying onset of pain. In still other embodiments, active agents comprise amphetamines.

A wide variety of spacers are known in the art, and include by way of example and not limitation, alkyl, heteroalkyl, acyclic heteroatomic bridges, aryl, arylaryl, arylalkyl, heteroaryl, heteroarylalkyl and the like. Thus, spacers may include, for example, single, double, triple or aromatic carbon-carbon bonds, nitrogen-nitrogen bonds, carbon-nitrogen, carbon-oxygen bonds and/or carbon-sulfur bonds, and may therefore include functionalities such as carbonyls, ethers, thioethers, carboxamides, sulfonamides, ureas, urethanes, hydrazines, etc. Examples of suitable spacers include, but are not limited to, aryl, biaryl, heteroaryl, etc. Where a flexible linker is desired, the linker may be a flexible peptide such as Gly-Gly-Gly or a flexible saturated alkanyl or heteroalkanyl. Hydrophilic linkers may be, for example, polyalcohols or polyethers such as polyalkyleneglycols. Hydrophobic linkers may be, for example, alkyls or aryls.

The cleavable moiety may comprise an amino acid, a peptide, an ester, a polyester, a thioester, a polythioester or any other cleavable group known to those of skill in the art. Generally, the cleavable moiety can be cleaved under physiological conditions. The cleavable moiety may be cleaved chemically (e.g., hydrolysis) or enzymatically. In some embodiments, the cleavable moiety is cleaved enzymatically. Generally, the compounds described herein are stable in aqueous solution, but not so stable that the cleavable moiety can not be cleaved chemically (e.g., hydrolysis) or enzymatically. In some embodiments, the cleavable moiety does not comprise an anhydride linkage. In some embodiments, the cleavable moiety does not comprise a substituted urea. In some embodiemts, the prodrug does not contain an ether linkage. In some embodiemts, the prodrug does not contain an aminobenzyl ether self-immolative group. In some embodiments, the prodrug does not contain a carboxylate linkage.

In a first embodiment, a compound of structural Formula (I) is provided

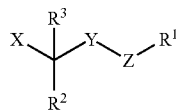
(I)

or salts, solvates or hydrates thereof wherein:

X is an active agent comprising an amine, phenol, carboxylic acid or thiol wherein a hydrogen atom of the primary or secondary amine, phenol, carboxylic acid or thiol is replaced by a covalent bond to —($CR^2R^3$)—Y-Z-$R^1$ or a lone pair of a tertiary amine is replaced by a covalent bond to —($CR^2R^3$)—Y-Z-$R^1$;

$R^2$ and $R^3$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

Y is aryl, heteroaryl or arylaryl optionally substituted with one or more —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ or —$C(NR^6)NR^5R^4$;

$R^4$, $R^5$, $R^6$ and $R^7$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^4$ and $R^5$ together with the nitrogen atom to which they are bonded form a cycloheteroalkyl or substituted cycloheteroalkyl ring;

Z is —N($R^8$)—, —O— or —S—;

$R^8$ is hydrogen, alkyl, substituted alkyl, aryl, substituted aryl, arylalkyl, substituted arylalkyl, heteroaryl, substituted heteroaryl, heteroarylalkyl, substituted heteroarylalkyl or

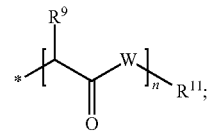

each W is independently —$NR^{10}$—, —O— or —S—;

each $R^9$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^9$ and $R^{10}$ together with the atoms to which they are bonded form a cycloheteroalkyl or substituted cycloheteroalkyl ring;

each $R^{10}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{10}$ and $R^{11}$ together with the atoms to which they are bonded form a cycloheteroalkyl or substituted cycloheteroalkyl ring;

$R^{11}$ is hydrogen, alkyl, substituted alkyl, aryl, substituted aryl, arylalkyl or substituted arylalkyl;

n is an integer from 0 to 5; or n is an integer from 1 to 5;

$R^1$ is

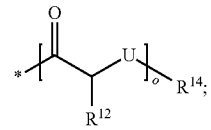

each U is independently —$NR^{13}$—, —O— or —S—;

each $R^{12}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl, or optionally, $R^{12}$ and $R^{13}$ together with the atoms to which they are bonded form a cycloheteroalkyl or substituted cycloheteroalkyl ring;

each $R^{13}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{13}$ and $R^{14}$ together with the atoms to which they are bonded form a cycloheteroalkyl or substituted cycloheteroalkyl ring;

$R^{14}$ is hydrogen, alkyl, substituted alkyl, acyl, substituted acyl, alkoxycarbonyl, substituted alkoxycarbonyl, aryl, substituted aryl, arylalkyl or substituted arylalkyl; and o is an integer from 1 to 5;

provided that Z is oriented para or ortho to X—($CR^2R^3$)—.

In some embodiments, $R^9$ is an amino acid side chain or analog thereof. In some embodiments, $R^9$ is —$CH_3$, $CH_2SH$, —$CH_2COOH$, —$CH_2CH_2COOH$, —$CH_2C_6H_5$, —$CH_2$—

$C_3H_3N_2$, —$CH(CH_3)CH_2CH_3$, —$(CH_2)_4NH_2$, —$CH_2CH(CH_3)_2$, —$CH_2CH_2SCH_3$, —$CH_2CONH_2$, —$CH_2CH_2CH_2$—, —$CH_2CH_2CONH_2$, —$(CH_2)_3NH$—$C(NH)NH_2$, —$CH_2OH$, —$CH(OH)CH_3$, —$CH(CH_3)_2$, —$CH_2C_8H_6N$, or —$CH_2$—$C_6H_4OH$.

In some embodiments, $R^{12}$ is an amino acid side chain or analog thereof. In some embodiments, $R^{12}$ is —$CH_3$, $CH_2SH$, —$CH_2COOH$, —$CH_2CH_2COOH$, —$CH_2C_6H_5$, —$CH_2$—$C_3H_3N_2$, —$CH(CH_3)CH_2CH_3$, —$(CH_2)_4NH_2$, —$CH_2CH(CH_3)_2$, —$CH_2CH_2SCH_3$, —$CH_2CONH_2$, —$CH_2CH_2CH_2$—, —$CH_2CH_2CONH_2$, —$(CH_2)_3NH$—$C(NH)NH_2$, —$CH_2OH$, —$CH(OH)CH_3$, —$CH(CH_3)_2$, —$CH_2C_8H_6N$, or —$CH_2$—$C_6H_4OH$.

In yet another embodiment, a compound of structural Formula (II) is provided:

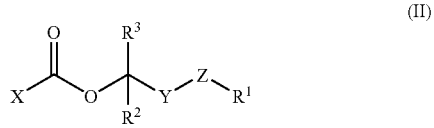

(II)

or salts, hydrates or solvates thereof wherein X, $R^1$, $R^2$, $R^3$, Y and Z are as previously defined provided that X is not a tertiary amine.

It should be understood that the description of various embodiments, infra, is applicable to compounds of structural Formula (I) and structural Formula (II).

In some embodiments, X is an opioid. As used herein an "opioid" is any substance that binds to or otherwise affects an opiate receptor. In other embodiments, X is morphine, codeine, diacetylmorphine, hydrocodone, hydromorphone, levorphanol, oxycodone, oxymorphone, naltrexone, nalbuphine, butorphanol, nalorphine, alfentanil, buprenorphine, carfentanil, codeine, diacetylmorphine, dihydrocodeine, dihydroetorphine, diprenorphine, etorphine, fentanyl, levomethadyl actetate hydrochloride, lofentanil, meperidine, methadone, morphine, naloxone, methyl naltrexone, beta-hydroxy 3-methylfentanyl, N-methylnaltrexone, normorphine, propoxyphene, remifentanil, sufentanil, tilidine, thebaine, nalmefene, neopine, penomorphone or tramadol. Other opioids may be found, for example, in the Physicians Desk Reference, 59th Edition, and the Merck Index, 13th Edition.

In other embodiments, X is amphetamine or derivative thereof. In other embodiments, X is dextroamphetamine, methamphetamine, p-methoxy amphetamine, methylenedioxyamphetamine, 2,5-dimethoxy-4-methylamphetamine, 2,4,5-trimethoxyamphetamine, hydroxyamphetamine, 3,4-methylenedioxyampheamine, methylphenidate, or D-methylphenidate.

In still other embodiments, X is acyclovir, adefovir dipivoxil, alendronate, albuterol, carbodopa, levodopa, amifostine, amlodipine besylate, astemizole, azathioprene, amoxicillin, (3R,5R)-1-butyl-3-ethyl-2,3,4,5-tetrahydro-7,8-dimethoxy-5-phenyl-1,4benzothiazepine-1,1-dioxide, buprorion, cabergoline, carboplatin, cefpodoxime proxetil, cefprozil, chlordiazepoxide, (R)-2-chloro-5-(2-azetidinylmethoxy)pyridine, cisapride, cisplatin, clozapine, colestipol, cyclophosphamide, desmopressin, dolasetrom mesylate, doxazosin, duloxetine, famciclovir, famotidine, felodipine, flecainide acetate, fluoxetine, fluvoxamine maleate, hydrochlorothiazide, isradipine, lamotrigine, metolazone, naratriptan, nifedipine, nimodipine, nisoldipine, [2S-(2α,3α,5α)]-2-(3,5-difluorophenyl)-3,5-dimethyl-2-morpholinol hydrochloride, norastemizole, nortriptyline, octreotide acetate, olanzapine, pamidronate, paroxetine, pemoline, pergolide, pramipexole, remacemide, repinotan, riluzole, rimantadine, rizatriptan benzoate, satraplatin, sertraline, sevelamer, (5R)-5-(2,3,-dichlorophenyl)-6-(fluoromethyl)-2,4-pyrimidinediamine, sumatriptan, tabimorelin, tamsulosin, tenofovir disproxil, terazosin, tirapazamine, tizanidine, tomoxetine, topiramate, toresemide, triamterene, valacyclovir, valdecoxib, zolmitriptan, clarithromicin, clavulanate, arginine, baclofen, benazepril, bleomycin, carvedilol, caspofungin, cefaclor, cefadroxil, cephalexin, chondroitin, diclofenac, dopamine, enalapril, enoxparin, ergotamine, gabapentin, gemcitabine, glucosamine, huperzine, phenylpropanolamine, idarubicin, ilomastat, iodothyronine, thyroxine, ketotifen, labetalol, levothyroxine, lisinopril, loracarbef, mefloquine, mesalamine, metoprolol, nadololnelarabine, norflaxacin, pregabalin, propranolol, pseudoephedrine, quinapril, 1-cyclopropyl-8-(difluoromethoxy)-7-[(1R)-2,3-dihydro-1-methyl-1H-isoindol-5-yl]-1,4-dihydro-4-oxo-3-quinolinecarboxylic acid, rampipril, sitafloxacin, tirofiban, tobramycin, trandolapril, trovafloxacin, hydroxytryptophan, methyldopa, 3-O-methyldopa, N-methylepinephrine, epinephrine, milnaciprin, cephalexin, dopamine, mefloquine, metoprolol, psuedoephedrine, propranol, tirofiban, tobramycin, muscimol, neopine, nordefrin, tirofiban, norepinephrine, nelfanivir, norpsuedoepinephrine, phentermine, phenylephrine, phenylpropanolamine, pholedrine, pindolol, pipradol, practolol, procaine, soltalol, synephrine, terbutaline, terodiline, tranylcypromine or vancomycin. Other physiologically active amines may be found, for example, in the Physicians Desk Reference, 59th Edition, and the Merck Index, 13th Edition.

In still other embodiments, X is the carboxylic acid selected from the group consisting of acteylsalicylic acid, acitretin, candoxatril, cefazolin, cefdinir, cefixime, cefotaxime, cefotetan, cefoxitin, ceftazidime, ceftibuten, cefuroxime, cetirizine, chloroazepate depot, [1S-[1α,2β[S*(S*)]4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-butanoic acid, cilomilast, divalproex, eptifibatide, etodolac, etoposide, fexofenadine, fosinopril, furosemide, gemfibrozil, ibuprofen, isotrtinoin, isradipine, ketoprofen, ketorolac, levocarnitine, levcetirizine, levofloxacin, meropenem, mitiglinide, montelukast, fexfenadine, naproxen, ofloxacin, oxaprozin, pemetrexed, penicillin V, piperacillin, repaglinide, tiagabine, valproic acid, valsartan, zenarestat, alporstadil, [S-(R*,R*)]-hexahydro-6-[(2-mercapto-1-oxo-3-phenylpropyl)amino]-2,2-dimethyl-7-oxo-1H-azepine, amoxicillin, clavulanate, arginine, baclofen, benazepril, carbidopa, levodopa, captopril, cefaclor, cefadroxil, cephalexin, cerivastin, imipenem, ciprofloxcin, diclofenac, doxorubicin, enalapril, enoxparin, fluvastin, gabapentin, ibuprofen, iodothyronine, thyroxine, ketotifen, levothyroxine, lisinopril, loracarbef, mesalamine, moexipril, norflaxacin, pravastatin, pregabalin, quinapril, 1-cyclopropyl-8-(difluoromethoxy)-7-[(1R)-2,3-dihydro-1-methyl-1H-isoindol-5-yl]-1,4-dihydro-4-oxo-3-quinolinecarboxylic acid, rampipril, sitafloxacin, sparfosic acid, trandolapril, trovafloxacin, ursodiol and vancomycin. Other physiologically active carboxylic acids may be found, for example, in the Physicians Desk Reference, 59th Edition, and the Merck Index, 13th Edition.

In still other embodiments, X is the thiol selected from the group consisting of penicillamine, enalapril, captopril, N-acetyl cysteine, bucillamine and 6-mercaptopurine. Other physiologically active thiols may be found, for example, in the Physicians Desk Reference, 59th Edition and the Merck Index, 13th Edition.

In still other embodiments, X is the phenol selected from the group consisting of fenoldopam, hydromorphone, acetaminophen, nelfinavir, morphine, epinephrine, propofol, fulvestrant, quinupristin, mesalamine, butorphanol, edrophonium chloride, labetalol, phenylephrine, nalmefene, plicamycin, leuprolide, duanorubicin, estradiol, metaproterenol, albuterol, cefprozil, carbodopa, levodopa, valrubicin, iodoquinol, naloxone, oxymorphone, nalbuphine, levothyroxine, malarone/atovaquone, salmeterol, mitoxantrone, aminosalicylic acid, liothyronine, raloxifene, vancomycin, pirbuterol, hydroquinone, mitocycline, ciclopirox, methyldopa, metarminol, caspofungin, capsaicin, resiniferotoxin, metyrosine, diflunisal, estradiol, entacapone, formoterol, doxycycline, ganirelix acetate, piroxicam, sulfasalazine, tolterodine, epirubicin, idarubicin, mesalaamine, labetalol, buprenorphine, balsalazide, nafarelin acetate, cetrorelix, anthralin, amoxicillin, dronabinol, minocycline, etorphine, levorphanol, naltrexone, nalorphine, buprenorphine, diprenorphine, morphine and olsalazine. Other physiologically active phenols may be found, for example, in the Physicians Desk Reference, 59th Edition and the Merck Index, 13th Edition.

In some embodiments, $R^2$ and $R^3$ are independently hydrogen, alkyl, alkoxy, aryl, substituted aryl, arylalkyl, heteroaryl or heteroarylalkyl. In other embodiments, $R^2$ and $R^3$ are independently hydrogen, alkyl, aryl, substituted aryl or arylalkyl. In still other embodiments, $R^2$ and $R^3$ are independently hydrogen, alkyl, or aryl.

In some embodiments, Y is phenyl, naphthyl, anthracenyl or biphenyl. In other embodiments, Y is pyridyl, indolyl, quinolinyl or isoquinolinyl. In still other embodiments, Y is optionally substituted with one or more —F, —Cl, —Br, —I, —$R^4$, —$OR^4$, —$SR^4$, —$NR^4R^5$, —$CF_3$, —CN, —$NO_2$, —$N_3$, —$S(O)_2O^-$, —$S(O)_2OH$, —$S(O)_2R^4$, —$P(O)(O^-)_2$, —$P(O)(OR^4)(O^-)$, —$OP(O)(OR^4)(OR^5)$, —$C(O)R^4$, —$C(O)OR^4$, —$C(O)NR^4R^5$ or —$C(O)O^-$. In still other embodiments, Y is phenyl, naphthyl, anthracenyl, biphenyl, pyridyl, indolyl, quinolinyl or isoquinolinyl optionally substituted with one or more —F, —Cl, —Br, —I, —$R^4$, —$OR^4$, —$SR^4$, —$NR^4R^5$, —$CF_3$, —CN, —$NO_2$, —$N_3$, —$S(O)_2O^-$, —$S(O)_2OH$, —$S(O)_2R^4$, —$P(O)(O^-)_2$, —$P(O)(OR^4)(O^-)$, —$OP(O)(OR^4)(OR^5)$, —$C(O)R^4$, —$C(O)OR^4$, —$C(O)NR^4R^5$ or —$C(O)O^-$.

In some embodiments, Z is —$N(R^8)$— and $R^8$ is hydrogen or alkyl, aryl or arylalkyl. In other embodiments, Z is —$N(R^8)$— and $R^8$ is

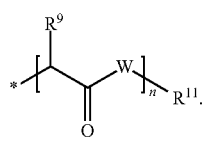

In some embodiments, each $R^9$ is independently, an amino acid side chain, hydrogen, alkanyl, substituted alkanyl, aryl, arylalkanyl, cycloalkanyl, substituted cycloalkanyl, substituted arylalkanyl or heteroarylalkanyl or optionally, each $R^9$ and $R^{10}$ independently, together with the atoms to which they are attached form a cycloheteroalkanyl or substituted cycloheteroalkanyl ring. In other embodiments, each $R^9$ is independently, hydrogen, methyl, isopropyl, isobutyl, sec-butyl, t-butyl, cyclopentyl, cyclohexyl, —$CH_2OH$, —CH(OH) $CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, homobenzyl, 4-hydroxybenzyl, 4-bromobenzyl, 4-imidazolylmethyl, 3-indolylmethyl, 3-[5-hydroxyindolyl]-methyl, 9-anthranylmethyl, 3-benzothienylmethyl, cyclohexylmethyl, diphenylmethyl, 2-furylmethyl, iodomethyl, 1-napthylmethyl, 2-napthylmethyl, 2-pyridylmethyl, 3-pyridylmethyl, 4-pyridylmethyl, 3-styrylmethyl, 2-thienylmethyl, vinylmethyl, cyclohexyl, acetylenomethyl, 2-trifluoromethylbenzyl, 2-chlorobenzyl, 2-cyanobenzyl, 2-fluorobenzyl, 2-methylbenzyl, 3-trifluoromethylbenzyl, 3-chlorobenzyl, 3-cyanobenzyl, 3-fluorobenzyl, 3-methylbenzyl, 4-benzoylbenzyl, 3,5 dibromo-4-hydroxybenzyl, 3-trifluoromethylbenzyl, 4-chlorobenzyl, 4-cyanobenzyl, 4-fluorobenzyl, 4-iodobenzyl, 4-methylbenzyl, 4-nitrobenzyl, 3,4-dihydroxybenzyl, 2,4 dichlorobenzyl, 3,4 dichlorobenzyl, 3,4 difluorobenzyl, 3,5 diiodo-4-hydroxylbenzyl, 3-nitro-4-hydroxybenzyl, aminomethyl,

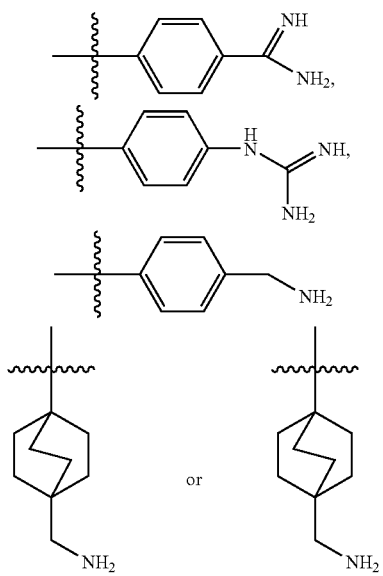

or optionally each $R^9$ and $R^{10}$, independently together with the atoms to which they are attached form an azetidine, pyrrolidine or piperidine ring. In still other embodiments, W is —$NR^{10}$ and each $R^{10}$ is independently hydrogen or alkyl, aryl or arylalkyl. In still other embodiments, $R^{11}$ is hydrogen, alkyl, acyl or alkoxycarbonyl.

In some embodiments, each $R^9$ is independently hydrogen, methyl, isopropyl, isobutyl, sec-butyl, t-butyl, cyclopentyl, cyclohexyl, —$CH_2OH$, —CH(OH)$CH_3$, —$CH_2CONH_2$, —$CH_2CH_2SCH_3$, —$CH_2SH$, phenyl, benzyl, 4-hydroxybenzyl, 4-bromobenzyl or 3-indolylmethyl. In other embodiments, each $R^9$ is independently hydrogen, methyl, isopropyl, isobutyl, sec-butyl, t-butyl, cyclopentyl, cyclohexyl, phenyl, benzyl, 4-bromobenzyl, 3-indolylmethyl or optionally each $R^9$ and $R^{10}$, independently together with the atoms to which they are attached form an azetidine, pyrrolidine or piperidine ring. In some of these embodiments, each W is —$NR^{10}$, each $R^{10}$ is hydrogen or optionally each $R^9$ and $R^{10}$, independently together with the atoms to which they are attached form an azetidine, pyrrolidine or piperidine ring and $R^{11}$ is hydrogen.

In some embodiments, each $R^9$ is independently —$CH_2(CH_2)_3NH_2$, —$CH_2CH_2CH_2NHC(NH)NH_2$, 4-imidazolylmethyl,

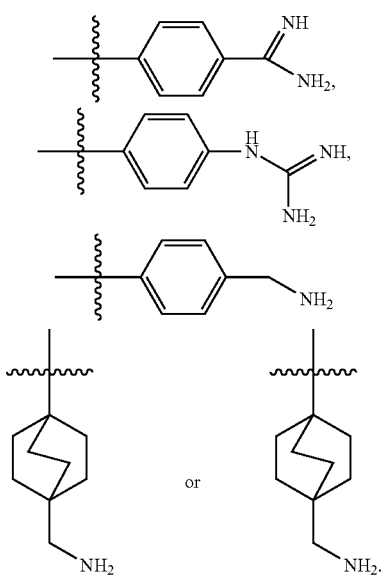

In some embodiments, each W is —NR$^{10}$—, each R$^{10}$ is hydrogen or optionally each R$^9$ and R$^{10}$, independently together with the atoms to which they are attached form an azetidine, pyrrolidine or piperidine ring and R$^{11}$ is hydrogen. In some embodiments, R$^1$ is hydrogen.

In some embodiments, n=2 and the R$^9$ group adjacent to the active agent is benzyl, isobutyl or R$^9$ and R$^{10}$, independently together with the atoms to which they are attached form a pyrrolidine ring and the other R$^9$ group is independently, hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, homobenzyl, 4-hydroxybenzyl, 4-bromobenzyl, 4-imidazolylmethyl, 3-indolylmethyl, 3-[5-hydroxyindolyl]-methyl, 9-anthranylmethyl, 3-benzothienylmethyl, cyclohexylmethyl, diphenylmethyl, 2-furylmethyl, iodomethyl, 1-napthylmethyl, 2-napthylmethyl, 2-pyridylmethyl, 3-pyridylmethyl, 4-pyridylmethyl, 3-styrylmethyl, 2-thienylmethyl, vinylmethyl, cyclohexyl, acetylenomethyl, 2-trifluoromethylbenzyl, 2-chlorobenzyl, 2-cyanobenzyl, 2-fluorobenzyl, 2-methylbenzyl, 3-trifluoromethylbenzyl, 3-chlorobenzyl, 3-cyanobenzyl, 3-fluorobenzyl, 3-methylbenzyl, 4-benzoylbenzyl, 3,5 dibromo-4-hydroxybenzyl, 3-trifluoromethylbenzyl, 4-chlorobenzyl, 4-cyanobenzyl, 4-fluorobenzyl, 4-iodobenzyl, 4-methylbenzyl, 4-nitrobenzyl, 3,4-dihydroxybenzyl, 2,4 dichlorobenzyl, 3,4 dichlorobenzyl, 3,4 difluorobenzyl, 3,5 diiodo-4-hydroxylbenzyl, 3-nitro-4-hydroxybenzyl, aminomethyl,

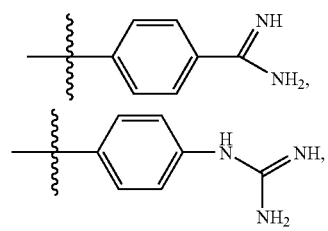

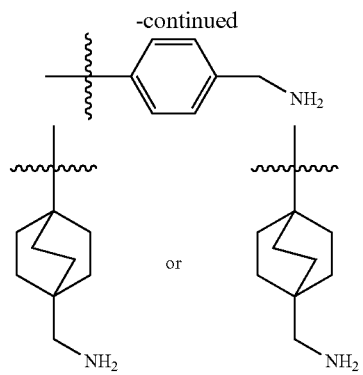

or optionally each R$^9$ and R$^{10}$, independently together with the atoms to which they are attached form an azetidine, pyrrolidine or piperidine ring. In some embodiments, each W is —NR$^{10}$—, each R$^{10}$ is hydrogen or optionally each R$^9$ and R$^{10}$, independently together with the atoms to which they are attached form an pyrrolidine ring and R$^{11}$ is hydrogen. In some embodiments, R$^1$ is hydrogen.

In some embodiments, each R$^{12}$ is independently, hydrogen, an amio acid side chain, alkanyl, substituted alkanyl, aryl, arylalkanyl, cycloalkanyl, substituted cycloalkanyl, substituted arylalkanyl or heteroarylalkanyl or optionally, each R$^{12}$ and R$^{13}$ independently, together with the atoms to which they are attached form a cycloheteroalkanyl or substituted cycloheteroalkanyl ring. In other embodiments, each R$^{12}$ is independently, hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, homobenzyl, 4-hydroxybenzyl, 4-bromobenzyl, 4-imidazolylmethyl, 3-indolylmethyl, 3-[5-hydroxyindolyl]-methyl, 9-anthranylmethyl, 3-benzothienylmethyl, cyclohexylmethyl, diphenylmethyl, 2-furylmethyl, iodomethyl, 1-napthylmethyl, 2-napthylmethyl, 2-pyridylmethyl, 3-pyridylmethyl, 4-pyridylmethyl, 3-styrylmethyl, 2-thienylmethyl, vinylmethyl, cyclohexyl, acetylenomethyl, 2-trifluoromethylbenzyl, 2-chlorobenzyl, 2-cyanobenzyl, 2-fluorobenzyl, 2-methylbenzyl, 3-trifluoromethylbenzyl, 3-chlorobenzyl, 3-cyanobenzyl, 3-fluorobenzyl, 3-methylbenzyl, 4-benzoylbenzyl, 3,5 dibromo-4-hydroxybenzyl, 3-trifluoromethylbenzyl, 4-chlorobenzyl, 4-cyanobenzyl, 4-fluorobenzyl, 4-iodobenzyl, 4-methylbenzyl, 4-nitrobenzyl, 3,4-dihydroxybenzyl, 2,4 dichlorobenzyl, 3,4 dichlorobenzyl, 3,4 difluorobenzyl, 3,5 diiodo-4-hydroxylbenzyl, 3-nitro-4-hydroxybenzyl, aminomethyl,

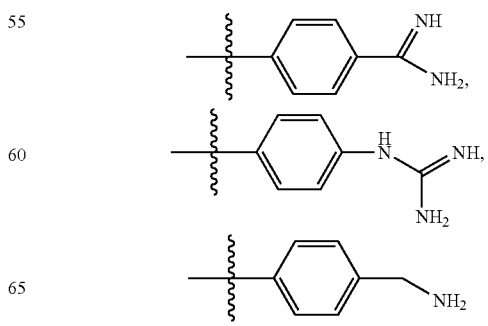

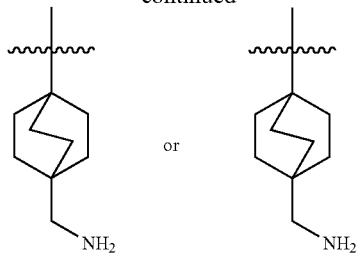

or optionally each $R^9$ and $R^{10}$, independently together with the atoms to which they are attached form an azetidine, pyrrolidine or piperidine ring.

In some embodiments, W is —$NR^{13}$ and each $R^{13}$ is independently hydrogen or alkyl, aryl or arylalkyl. In other embodiments, $R^{14}$ is hydrogen, alkyl, acyl or alkoxycarbonyl. In still other embodiments, each $R^{12}$ is independently methyl, benzyl, —$CH_2CO_2H$, —$CH_2(CH_2)_3NH_2$ or —$CH_2CH_2CH_2NHC(NH)NH_2$.

In some embodiments, o is 1 and $R^{12}$ is methyl, benzyl, —$CH_2CO_2H$, —$CH_2(CH_2)_3NH_2$ or —$CH_2CH_2CH_2NHC(NH)NH_2$. In some embodiments, o is 1 and $R^{12}$ is phenyl, benzyl, 4-hydroxybenzyl, 4-bromobenzyl, 4-imidazolylmethyl, 3-indolylmethyl, isobutyl, —$CH_2CH_2SCH_3$, —$CH_2CH_2CONH_2$ or —$CH_2CH_2CONH_2$. In some embodiments, o is 1 and $R^{12}$ is benzyl, 4-hydroxybenzyl, 4-bromobenzyl, 4-imidazolylmethyl or 3-indolylmethyl. In other embodiments, each U is —$NR^{13}$—, each $R^{13}$ is hydrogen and $R^{14}$ is hydrogen, acyl, substituted acyl, alkoxycarbonyl or substituted alkoxycarbonyl. In some of the above embodiments, $R^8$ is hydrogen or methyl.

In some embodiments, each $R^{12}$ is independently phenyl, 4-hydroxybenzyl, 4-bromobenzyl, 4-imidazolylmethyl, 3-indolylmethyl, isobutyl, —$CH_2CH_2SCH_3$, —$CH_2CH_2CONH_2$ or —$CH_2CH_2CONH_2$. In other embodiments, each $R^{12}$ is independently 4-hydroxybenzyl, 4-bromobenzyl or 3-indolylmethyl. In still other embodiments, o is 1 and $R^{12}$ is phenyl, 4-hydroxybenzyl, 4-bromobenzyl, 4-imidazolylmethyl, 3-indolylmethyl, isobutyl, —$CH_2CH_2SCH_3$, —$CH_2CH_2CONH_2$, or —$CH_2CH_2CONH_2$. In still other embodiments, o is 1 and $R^{12}$ is 4-hydroxybenzyl, 4-bromobenzyl or 3-indolylmethyl. In some of the above embodiments, each U is —$NR^{13}$—, each $R^{13}$ is hydrogen and $R^{14}$ is acyl, substituted acyl, alkoxycarbonyl or substituted alkoxycarbonyl. In some of the above embodiments, $R^8$ is hydrogen or methyl.

In some embodiments, o is greater than 1 and $R^{14}$ is hydrogen. In other embodiments, each U is —$NR^{13}$—, each $R^{13}$ is hydrogen and $R^{14}$ is acyl, substituted acyl, alkoxycarbonyl or substituted alkoxycarbonyl. In some of the above embodiments, $R^8$ is hydrogen or methyl.

In some embodiments, o is 3 and $R^{14}$ is hydrogen. In other embodiments, each U is —$NR^{13}$— and each $R^{13}$ is hydrogen. In some of the above embodiments, $R^8$ is hydrogen or methyl.

In some embodiments, each $R^{12}$ is independently hydrogen, methyl, isopropyl, isobutyl, sec-butyl, —$CH_2OH$ or —$CH_2SH$. In other embodiments, n is 1 and $R^{12}$ is hydrogen, methyl, isopropyl, isobutyl or sec-butyl. In some of the above embodiments, each U is —$NR^{13}$—, each $R^{13}$ is hydrogen and $R^{14}$ is acyl, substituted acyl, alkoxycarbonyl or substituted alkoxycarbonyl. In some of the above embodiments, $R^8$ is hydrogen or methyl.

In some embodiments, each $R^{12}$ is independently hydrogen, methyl, isopropyl, isobutyl, sec-butyl, t-butyl, cyclopentyl, cyclohexyl, —$CH_2OH$, —$CH(OH)CH_3$, —$CH_2CONH_2$, —$CH_2CH_2SCH_3$, —$CH_2SH$, phenyl, benzyl, 4-hydroxybenzyl, 4-bromobenzyl or 3-indolylmethyl. In other embodiments, each $R^9$ is independently hydrogen, methyl, isopropyl, isobutyl, sec-butyl, t-butyl, cyclopentyl, cyclohexyl, phenyl, benzyl, 4-bromobenzyl, 3-indolylmethyl or optionally each $R^9$ and $R^{10}$, independently together with the atoms to which they are attached form an azetidine, pyrrolidine or piperidine ring. In some of the above embodiments, each U is —$NR^{13}$—, each $R^{13}$ is hydrogen or optionally each $R^{12}$ and $R^{13}$, independently together with the atoms to which they are attached form an azetidine, pyrrolidine or piperidine ring and $R^{14}$ is acyl, substituted acyl, alkoxycarbonyl or substituted alkoxycarbonyl. In some of the above embodiments, $R^8$ is hydrogen or methyl.

In some embodiments, each $R^{12}$ is independently benzyl, 4-hydroxybenzyl or isobutyl. In some embodiments, each U is —$NR^{13}$—, each $R^{13}$ is hydrogen and $R^{14}$ is acyl, substituted acyl, alkoxycarbonyl or substituted alkoxycarbonyl. In some embodiments, $R^8$ is hydrogen or methyl.

In some embodiments, each $R^{12}$ is independently —$CH_2CO_2H$ or —$CH_2CH_2CO_2H$. In other embodiments, each U is —$NR^{13}$—, each $R^{13}$ is hydrogen and $R^{14}$ is acyl, substituted acyl, alkoxycarbonyl or substituted alkoxycarbonyl. In some of the above embodiments, $R^8$ is hydrogen or methyl.

In some embodiments, o=2 and the $R^{12}$ group adjacent to the active agent is independently, hydrogen, methyl, isopropyl, isobutyl, sec-butyl, t-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, homobenzyl, 4-hydroxybenzyl, 4-bromobenzyl, 4-imidazolylmethyl, 3-indolylmethyl, 3-[5-hydroxyindolyl]-methyl, 9-anthranylmethyl, 3-benzothienylmethyl, cyclohexylmethyl, diphenylmethyl, 2-furylmethyl, iodomethyl, 1-napthylmethyl, 2-napthylmethyl, 2-pyridylmethyl, 3-pyridylmethyl, 4-pyridylmethyl, 3-styrylmethyl, 2-thienylmethyl, vinylmethyl, cyclohexyl, acetylenomethyl, 2-trifluoromethylbenzyl, 2-chlorobenzyl, 2-cyanobenzyl, 2-fluorobenzyl, 2-methylbenzyl, 3-trifluoromethylbenzyl, 3-chlorobenzyl, 3-cyanobenzyl, 3-fluorobenzyl, 3-methylbenzyl, 4-benzoylbenzyl, 3,5 dibromo-4-hydroxybenzyl, 3-trifluoromethylbenzyl, 4-chlorobenzyl, 4-cyanobenzyl, 4-fluorobenzyl, 4-iodobenzyl, 4-methylbenzyl, 4-nitrobenzyl, 3,4-dihydroxybenzyl, 2,4 dichlorobenzyl, 3,4 dichlorobenzyl, 3,4 difluorobenzyl, 3,5 diiodo-4-hydroxylbenzyl, 3-nitro-4-hydroxybenzyl, aminomethyl,

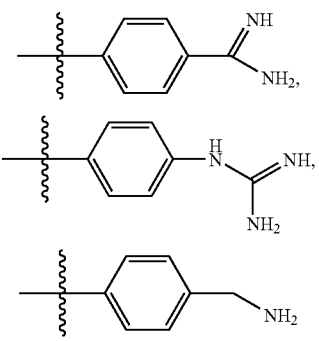

-continued

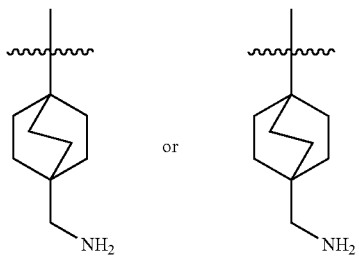

or optionally each $R^{12}$ and $R^{13}$, independently together with the atoms to which they are attached form an azetidine, pyrrolidine or piperidine ring and the other $R^{12}$ group is methyl or $R^{12}$ and $R^{13}$, independently together with the atoms to which they are attached form a pyrrolidine ring. In other embodiments, U is —$NR^{13}$—, each $R^{13}$ is hydrogen or optionally each $R^{12}$ and $R^{13}$, independently together with the atoms to which they are attached form an pyrrolidine ring and $R^{14}$ is acyl, substituted acyl, alkoxycarbonyl or substituted alkoxycarbonyl.

In some embodiments, $R^8$ is hydrogen or methyl, and o is 3. In some embodiments $R^8$ is hydrogen, $R^1$ is

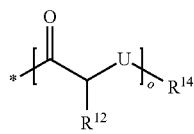

and o is 3.

In some embodiments, $R^8$ is

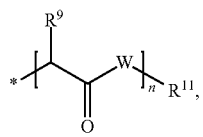

n is 2 and o is 1. In embodiments $R^8$ is

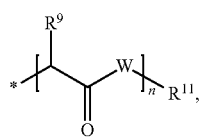

n is 2, $R^1$ is

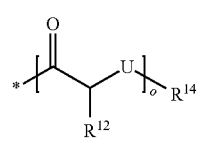

and o is 1.

In some embodiments, $R^8$ is

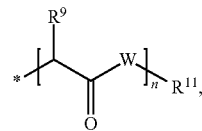

n is 1 and o is 2. In some emodiemnts, $R^8$ is

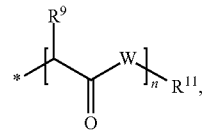

n is 1, $R^1$ is

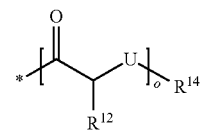

and o is 2.

In some embodiments, X is an opioid, an opioid with a phenolic functionality or an amphetamine, $R^2$ and $R^3$ are independently hydrogen, alkyl, aryl or arylalkyl, Y is phenyl, naphthyl, anthracenyl or biphenyl, optionally substituted with one or more —F, —Cl, —Br, —I, —$R^3$, —$OR^3$, —$SR^3$, —$NR^3R^4$, —$CF_3$, —CN, —$NO_2$, —$N_3$, —$S(O)_2O^-$, —$S(O)_2OH$, —$S(O)_2R^3$, —$P(O)(O^-)_2$, —$P(O)(OR^2)(O^-)$, —$OP(O)(OR^3)(OR^3)$, —$C(O)R^3$, —$C(O)OR^3$, —$C(O)NR^3R^4$, or —$C(O)O^-$, Z is —$N(R^8)$—; $R^{10}$ is hydrogen, alkyl, aryl or arylalkyl; each $R^9$ is independently, hydrogen, alkanyl, substituted alkanyl, aryl, arylalkanyl, cycloalkanyl, substituted cycloalkanyl, substituted arylalkanyl or heteroarylalkanyl or optionally, each $R^9$ and $R^{10}$ independently, together with the atoms to which they are attached form a cycloheteroalkanyl or substituted cycloheteroalkanyl ring, $R^{13}$ is hydrogen, alkyl, aryl or arylalkyl and each $R^{12}$ is independently, hydrogen, alkanyl, substituted alkanyl, aryl, arylalkanyl, cycloalkanyl, substituted cycloalkanyl, substituted arylalkanyl or heteroarylalkanyl or optionally, each $R^{12}$ and $R^{13}$ independently, together with the atoms to which they are attached form a cycloheteroalkanyl or substituted cycloheteroalkanyl ring. In other embodiments, $R^2$ and $R^3$ are hydrogen, Y is optionally substituted phenyl, $R^8$ is hydrogen, alkyl, aryl or

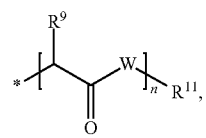

W is —$NR^{10}$— or —O—; $R^{10}$ is hydrogen, alkyl, aryl or optionally, each $R^9$ and $R^{10}$ independently, together with the atoms to which they are attached form a pyrrolidine ring, U is —$NR^{13}$—, $R^{13}$ is hydrogen, alkyl or aryl or optionally, each $R^{13}$ and $R^{14}$ independently, together with the atoms to which they are attached form a pyrrolidine ring and $R^{14}$ is hydrogen, acyl, substituted acyl, alkoxycarbonyl or substituted alkoxycarbonyl.

In some embodiments, $R^2$ and $R^3$ are hydrogen, Y is optionally substituted phenyl, $R^8$ is hydrogen, methyl or

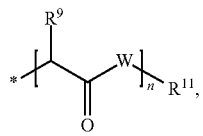

W is —$NR^{10}$— or —O—; $R^{10}$ is hydrogen, or optionally, each $R^9$ and $R^{10}$ independently, together with the atoms to which they are attached form a pyrrolidine ring, $R^{11}$ is hydrogen, alkyl or substituted alkyl, U is —$NR^{13}$—, $R^{13}$ is hydrogen or optionally, each $R^{13}$ and $R^{14}$ independently, together with the atoms to which they are attached form a pyrrolidine ring and $R^{14}$ is hydrogen, acyl, substituted acyl, alkoxycarbonyl or substituted alkoxycarbonyl. In still other embodiments, o is 1, $R^{12}$ is methyl, benzyl, —$CH_2CO_2H$, —$CH_2(CH_2)_3NH_2$ or —$CH_2CH_2CH_2NHC(NH)NH_2$ and $R^{13}$ is hydrogen. In some embodiments, $R^8$ is hydrogen or methyl. In other embodiments, $R^8$ is

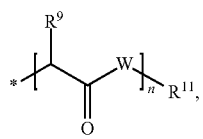

n is 1 or 2 and each $R^9$ is independently hydrogen, methyl, isopropyl, isobutyl, sec-butyl, t-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, homobenzyl, 4-hydroxybenzyl, 4-bromobenzyl, 4-imidazolylmethyl or 3-indolylmethyl and each $R^{10}$ is hydrogen.

In some embodiments, o is 2, $R^1$ is

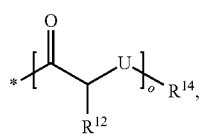

the $R^{12}$ closest to the opioid is —$CH_2(CH_2)_3NH_2$ or —$CH_2CH_2CH_2NHC(NH)NH_2$, the other $R^{12}$ is hydrogen, methyl, isopropyl, isobutyl, sec-butyl, t-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, homobenzyl, 4-hydroxybenzyl, 4-bromobenzyl, 4-imidazolylmethyl or 3-indolylmethyl, U is —$NR^{13}$ and each $R^{13}$ is hydrogen. In some of the above embodiments, $R^8$ is hydrogen or methyl.

In other embodiments, $R^8$ is

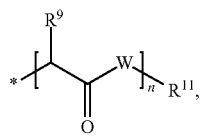

n is 1, $R^9$ is hydrogen, methyl, isopropyl, isobutyl, sec-butyl, t-butyl, cyclopentyl, cyclohexyl, —$CH_2OH$, —$CH(OH)$ $CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, homobenzyl, 4-hydroxybenzyl, 4-bromobenzyl, 4-imidazolylmethyl or 3-indolylmethyl and $R^{10}$ is hydrogen. In some embodiments, W is —O—.

In some embodiments, $R^2$ and $R^3$ are hydrogen and Y is phenyl. In other embodiments, $R^8$ is hydrogen or methyl, $R^{12}$ is methyl, benzyl, —$CH_2CO_2H$, —$CH_2(CH_2)_3NH_2$ or —$CH_2CH_2CH_2NHC(NH)NH_2$ and $R^{14}$ is hydrogen or —$CO_2$-t-butyl. In still other embodiments, $R^2$ and $R^3$ are hydrogen, Y is phenyl, $R^8$ is hydrogen or methyl, $R^{12}$ is methyl, benzyl, —$CH_2CO_2H$, —$CH_2(CH_2)_3NH_2$ or —$CH_2CH_2CH_2NHC(NH)NH_2$ and $R^{14}$ is hydrogen or —$CO_2$-t-butyl.

In any of the above embodiments, X is an opioid, such as, for example, morphine, codeine, diacetylmorphine, hydrocodone, hydromorphone, levorphanol, oxycodone, oxymorphone, naltrexone, nalbuphine, butorphanol, nalorphine, alfentanil, buprenorphine, carfentanil, codeine, diacetylmorphine, dihydrocodeine, dihydroetorphine, diprenorphine, etorphine, fentanyl, levomethadyl acetate hydrochloride, lofentanil, meperidine, methadone, morphine, naloxone, methylnaltrexone, beta-hydroxy 3-methylfentanyl, N-methylnaltrexone, normorphine, propoxyphene, remifentanil, sufentanil, tilidine, thebaine, nalmefene, neopine, penomorphone or tramadol. In some of any of the above embodiments, X is morphine, fentanyl, codeine, diacetylmorphine, etorphine, hydrocodone, hydromorphone, levorphanol, oxycodone, oxymorphone, naltrexone, nalbuphine, butorphanol or nalorphine. In other of any of the above embodiments, X is hydrocodone, hydromorphone, oxymorphone, oxycodone or codeine.

In any of the above embodiments, X is a phenolic opioid, such as, for example, oxymorphone, hydromorphone, buprenorphine, etorphine, levorphanol, naltrexone, nalorphine, diprenorphine, morphine, nalbuphine or butorphanol. In other of any of the above embodiments, X is oxymorphone or hydromorphone.

In any of the above embodiments, X is an amphetamine, such as, for example, amphetamine, dextroamphetamine, methamphetamine, p-methoxy amphetamine, methylenedioxyamphetamine, 2,5-dimethoxy-4-methylamphetamine, 2,4,5-trimethoxyamphetamine, 3,4-methylenedioxyamphetamine, methylphenidate or D-methylphenidate. In some of the above embodiments, X is dextroamphetamine, methylphenidate or D-methylphenidate.

In some embodiments, a compound of structural Formula (III) is provided:

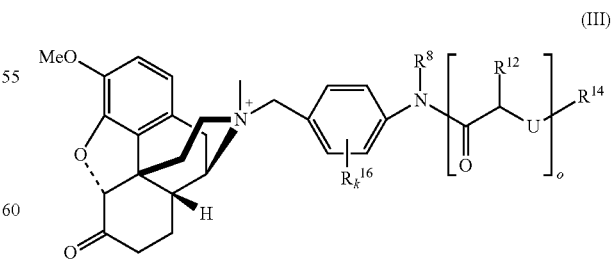

or salts, hydrates or solvates thereof wherein $R^8$ is hydrogen or methyl, $R^{12}$ is an amino acid side chain, $R^{14}$ is hydrogen, acetyl, or —$CO_2$-t-butyl, o is an integer from 1 to 5, $R_k^{16}$ are each independently selected from the group consisting of one or more of —F, —Cl, —Br, —I, —R⁴, —O⁻, —OR⁴, —SR⁴, —S⁻, —NR⁴R⁵, —CF₃, —CN, —OCN, —SCN, —NO, —NO₂, —N₃, —S(O)₂O⁻, —S(O)₂OH, —S(O)₂R⁴, —OS(O₂)O⁻, —OS(O)₂R⁴, —P(O)(O⁻)₂, —P(O)(OR⁴)(O⁻), —OP(O)(OR⁴)(OR⁵), —C(O)R⁴, —C(S)R⁴, —C(O)OR⁴, —C(O)NR⁴R⁵, —C(O)O⁻, —C(S)OR⁴, —NR⁶C(O)NR⁴R⁵, —NR⁶C(S)NR⁴R⁵, —NR⁷C(NR⁶)NR⁵R⁴ or —C(NR⁶)NR⁵R⁴, and k is 0, 1, 2, 3, or 4.

In some embodiments, a compound of structural Formula (IIIa) is provided:

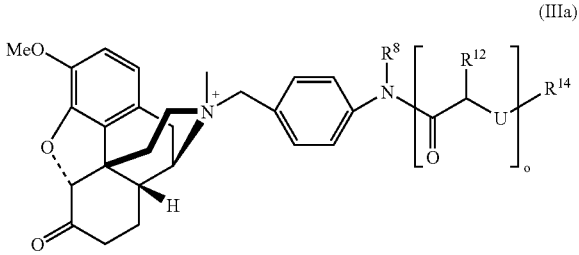

(IIIa)

or salts, hydrates or solvates thereof wherein wherein R⁸ is hydrogen or methyl, R¹² is an amino acid side chain, R¹⁴ is hydrogen, acyl, or —CO₂-t-butyl, and o is an integer from 1 to 5.

In other embodiments, a compound of structural Formula (IIIb) is provided:

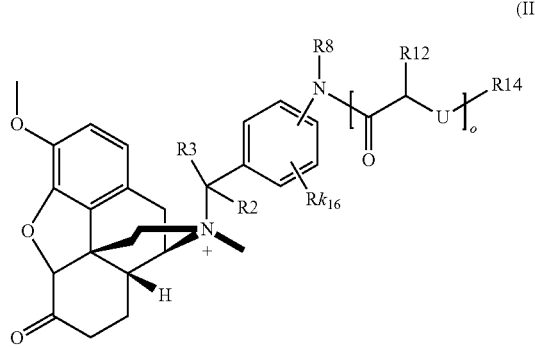

(IIIb)

or salts, hydrates or solvates thereof, wherein R² and R³ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl; R⁸ is hydrogen or methyl, R¹² is an amino acid side chain, R¹⁴ is hydrogen, acyl, or —CO₂-t-butyl, o is an integer from 1 to 5, $R_k^{16}$ are each independently selected from the group consisting of one or more of —F, —Cl, —Br, —I, —R⁴, —O⁻, —OR⁴, —SR⁴, —S⁻, —NR⁴R⁵, —CF₃, —CN, —OCN, —SCN, —NO, —NO₂, —N₃, —S(O)₂O⁻, —S(O)₂OH, —S(O)₂R⁴, —OS(O₂)O⁻, —OS(O)₂R⁴, —P(O)(O⁻)₂, —P(O)(OR⁴)(O⁻), —OP(O)(OR⁴)(OR⁵), —C(O)R⁴, —C(S)R⁴, —C(O)OR⁴, —C(O)NR⁴R⁵, —C(O)O⁻, —C(S)OR⁴, —NR⁶C(O)NR⁴R⁵, —NR⁶C(S)NR⁴R⁵, —NR⁷C(NR⁶)NR⁵R⁴ or —C(NR⁶)NR⁵R⁴, and k is 0, 1, 2, 3, or 4, provided that the substituent NR⁸ is oriented para or ortho to CR²R³.

In other embodiments, a structural Formula (IV) is provided:

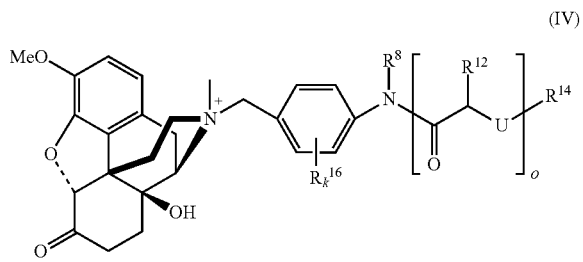

(IV)

or salts, hydrates or solvates thereof R⁸ is hydrogen or methyl, R¹² is an amino acid side chain, R¹⁴ is hydrogen, acyl, or —CO₂-t-butyl, o is an integer from 1 to 5, $R_k^{16}$ are each independently selected from the group consisting of one or more of —F, —Cl, —Br, —I, —R⁴, —O⁻, —OR⁴, —SR⁴, —S⁻, —NR⁴R⁵, —CF₃, —CN, —OCN, —SCN, —NO, —NO₂, —N₃, —S(O)₂O⁻, —S(O)₂OH, —S(O)₂R⁴, —OS(O₂)O⁻, —OS(O)₂R⁴, —P(O)(O⁻)₂, —P(O)(OR⁴)(O⁻), —OP(O)(OR⁴)(OR⁵), —C(O)R⁴, —C(S)R⁴, —C(O)OR⁴, —C(O)NR⁴R⁵, —C(O)O⁻, —C(S)OR⁴, —NR⁶C(O)NR⁴R⁵, —NR⁶C(S)NR⁴R⁵, —NR⁷C(NR⁶)NR⁵R⁴ or —C(NR⁶)NR⁵R⁴, and k is 0, 1, 2, 3, or 4.

In other embodiments, a structural Formula (IVa) is provided:

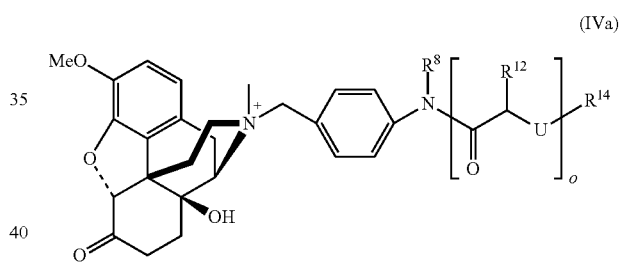

(IVa)

or salts, hydrates or solvates thereof R⁸ is hydrogen or methyl, R¹² is an amino acid side chain, R¹⁴ is hydrogen, acyl, or —CO₂-t-butyl, and o is an integer from 1 to 5.

In still other embodiments, a compound of structural Formula (VIb) is provided:

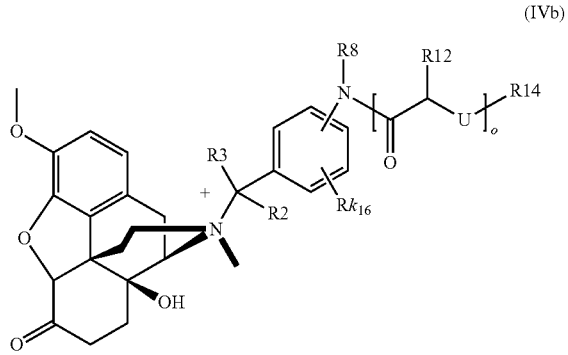

(IVb)

or salts, hydrates or solvates thereof, wherein R² and R³ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl; $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ or —$C(NR^6)NR^5R^4$, and k is 0, 1, 2, 3, or 4, provided that substituent $NR^8$ is oriented para or ortho to $CR^2R^3$.

In still other embodiments, a compound of structural Formula (V) is provided:

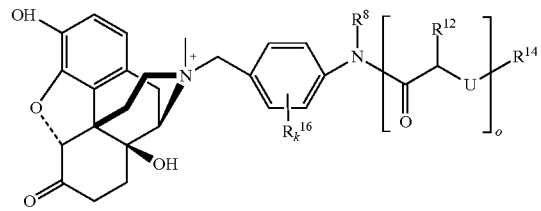

(V)

or salts, hydrates or solvates thereof $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ or —$C(NR^6)NR^5R^4$, and k is 0, 1, 2, 3, or 4.

In other embodiments, a compound of structural Formula (Va) is provided:

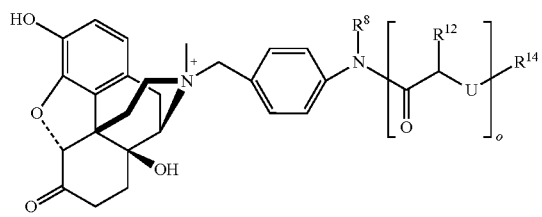

(Va)

or salts, hydrates or solvates thereof $R^8$ is hydrogen or methyl, $R^{12}$ is an amino acid side chain, $R^{14}$ is hydrogen, acyl, or —$CO_2$-t-butyl, and o is an integer from 1 to 5.

In still other embodiments, a compound of structural Formula (Vb) is provided:

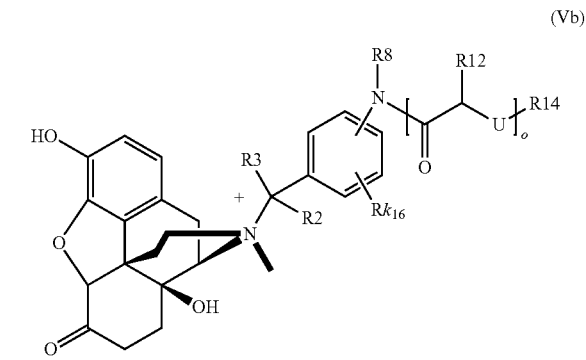

(Vb)

or salts, hydrates or solvates thereof, wherein $R^2$ and $R^3$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl; $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ or —$C(NR^6)NR^5R^4$, and k is 0, 1, 2, 3, or 4, provided that substituent $NR^8$ is oriented para or ortho to $CR^2R^3$.

In still other embodiments, a compound of structural Formula (VI) is provided:

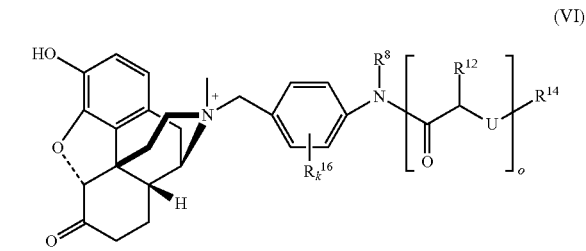

(VI)

or salts, hydrates or solvates thereof $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ or —$C(NR^6)NR^5R^4$, and k is 0, 1, 2, 3, or 4.

In still other embodiments, a compound of structural Formula (VIa) is provided:

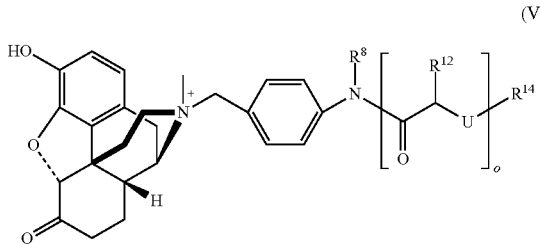

(VIa)

or salts, hydrates or solvates thereof $R^8$ is hydrogen or methyl, $R^{12}$ is an amino acid side chain, $R^{14}$ is hydrogen, acyl, or —CO$_2$-t-butyl, and 0 is an integer from 1 to 5.

In still other embodiments, a compound of structural Formula (VIb) is provided:

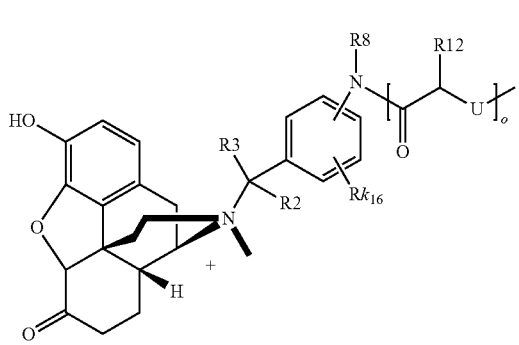

(VIb)

or salts, hydrates or solvates thereof, wherein $R^2$ and $R^3$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl; $R^8$ is hydrogen or methyl, $R^{12}$ is an amino acid side chain, $R^{14}$ is hydrogen, acyl, or —CO$_2$-t-butyl, o is an integer from 1 to 5, $R_k^{16}$ are each independently selected from the group consisting of one or more of —F, —Cl, —Br, —I, —R$^4$, —O$^-$, —OR$^4$, —SR$^4$, —S$^-$, —NR$^4$R$^5$, —CF$_3$, —CN, —OCN, —SCN, —NO, —NO$_2$, —N$_3$, —S(O)$_2$O$^-$, —S(O)$_2$OH, —S(O)$_2$R$^4$, —OS(O$_2$)O$^-$, —OS(O)$_2$R$^4$, —P(O)(O$^-$)$_2$, —P(O)(OR$^4$)(O$^-$), —OP(O)(OR$^4$)(OR$^5$), —C(O)R$^4$, —C(S)R$^4$, —C(O)OR$^4$, —C(O)NR$^4$R$^5$, —C(O)O$^-$, —C(S)OR$^4$, —NR$^6$C(O)NR$^4$R$^5$, —NR$^6$C(S)NR$^4$R$^5$, —NR$^7$C(NR$^6$)NR$^5$R$^4$ or —C(NR$^6$)NR$^5$R$^4$, and k is 0, 1, 2, 3, or 4, provided that substituent NR$^8$ is oriented para or ortho to CR$^2$R$^3$.

In still other embodiments, a compound of structural Formula (VII) is provided:

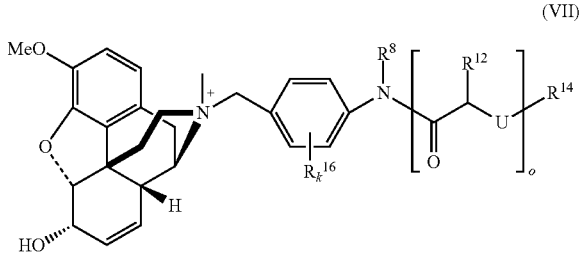

(VII)

or salts, hydrates or solvates thereof $R^8$ is hydrogen or methyl, $R^{12}$ is an amino acid side chain, $R^{14}$ is hydrogen, acyl, or —CO$_2$-t-butyl, o is an integer from 1 to 5, $R_k^{16}$ are each independently selected from the group consisting of one or more of —F, —Cl, —Br, —I, —R$^4$, —O$^-$, —OR$^4$, —SR$^4$, —S$^-$, —NR$^4$R$^5$, —CF$_3$, —CN, —OCN, —SCN, —NO, —NO$_2$, —N$_3$, —S(O)$_2$O$^-$, —S(O)$_2$OH, —S(O)$_2$R$^4$, —OS(O$_2$)O$^-$, —OS(O)$_2$R$^4$, —P(O)(O$^-$)$_2$, —P(O)(OR$^4$)(O$^-$), —OP(O)(OR$^4$)(OR$^5$), —C(O)R$^4$, —C(S)R$^4$, —C(O)OR$^4$, —C(O)NR$^4$R$^5$, —C(O)O$^-$, —C(S)OR$^4$, —NR$^6$C(O)NR$^4$R$^5$, —NR$^6$C(S)NR$^4$R$^5$, —NR$^7$C(NR$^6$)NR$^5$R$^4$ or —C(NR$^6$)NR$^5$R$^4$, and k is 0, 1, 2, 3, or 4.

In still other embodiments, a compound of structural Formula (VIIa) is provided:

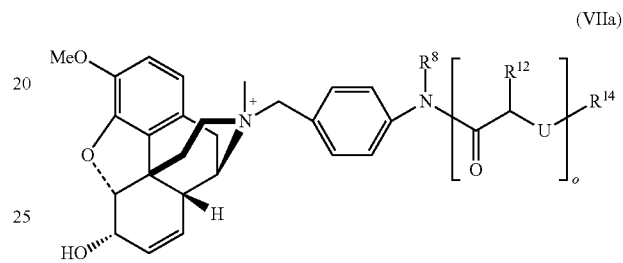

(VIIa)

or salts, hydrates or solvates thereof $R^8$ is hydrogen or methyl, $R^{12}$ is an amino acid side chain, $R^{14}$ is hydrogen, acyl, or —CO$_2$-t-butyl, and o is an integer from 1 to 5.

In still other embodiments, a compound of structural Formula (VIIb) is provided:

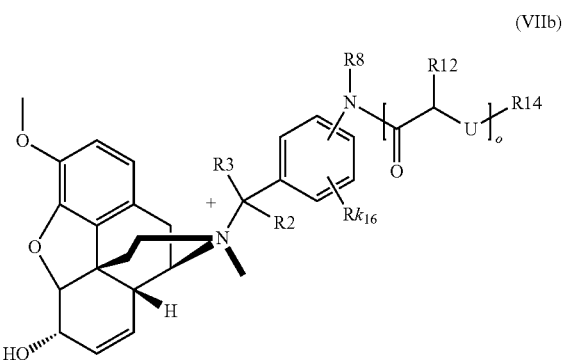

(VIIb)

or salts, hydrates or solvates thereof, wherein $R^2$ and $R^3$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl; $R^8$ is hydrogen or methyl, $R^{12}$ is an amino acid side chain, $R^{14}$ is hydrogen, acyl, or —CO$_2$-t-butyl, o is an integer from 1 to 5, $R_k^{16}$ are each independently selected from the group consisting of one or more of —F, —Cl, —Br, —I, —R$^4$, —O$^-$, —OR$^4$, —SR$^4$, —S$^-$, —NR$^4$R$^5$, —CF$_3$, —CN, —OCN, —SCN, —NO, —NO$_2$, —N$_3$, —S(O)$_2$O$^-$, —S(O)$_2$OH, —S(O)$_2$R$^4$, —OS(O$_2$)O$^-$, —OS(O)$_2$R$^4$, —P(O)(O$^-$)$_2$, —P(O)(OR$^4$)(O$^-$), —OP(O)(OR$^4$)(OR$^5$), —C(O)R$^4$, —C(S)R$^4$, —C(O)OR$^4$, —C(O)NR$^4$R$^5$, —C(O)O$^-$, —C(S)OR$^4$, —NR$^6$C(O)NR$^4$R$^5$, —NR$^6$C(S)NR$^4$R$^5$, —NR$^7$C(NR$^6$)NR$^5$R$^4$ or —C(NR$^6$)NR$^5$R$^4$, and k is 0, 1, 2, 3, or 4, provided that substituent NR$^8$ is oriented para or ortho to CR$^2$R$^3$.

In some embodiments, a compound of structural Formula (VIII) is provided:

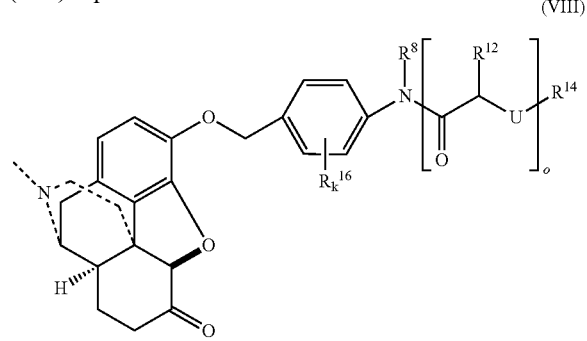
(VIII)

or salts, hydrates or solvates thereof $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ or —$C(NR^6)NR^5R^4$, and k is 0, 1, 2, 3, or 4.

In some embodiments, a compound of structural Formula (VIIIa) is provided:

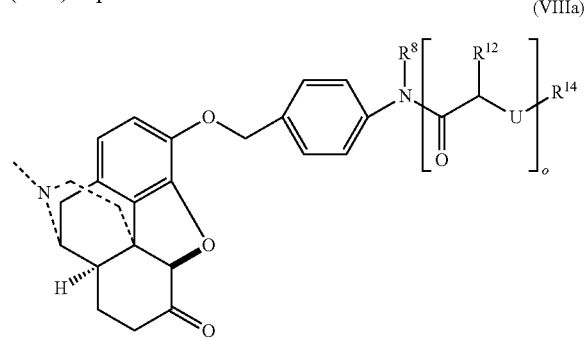
(VIIIa)

or salts, hydrates or solvates thereof $R^8$ is hydrogen or methyl, $R^{12}$ is an amino acid side chain, $R^{14}$ is hydrogen, acyl, or —$CO_2$-t-butyl, and o is an integer from 1 to 5.

In still other embodiments, a compound of structural Formula (VIIIb) is provided:

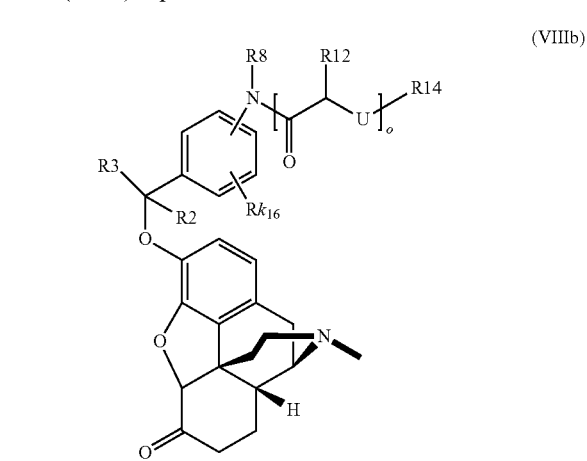
(VIIIb)

or salts, hydrates or solvates thereof, wherein $R^2$ and $R^3$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl; $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ or —$C(NR^6)NR^5R^4$, and k is 0, 1, 2, 3, or 4, provided that substituent $NR^8$ is oriented para or ortho to $CR^2R^3$.

In other embodiments, a compound of structural Formula (IX) is provided:

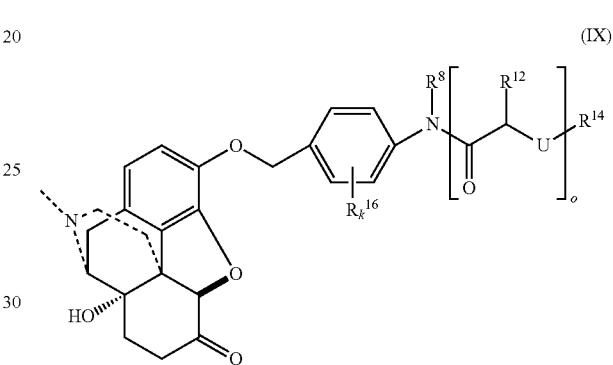
(IX)

or salts, hydrates or solvates thereof $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ or —$C(NR^6)NR^5R^4$, and k is 0, 1, 2, 3, or 4.

In other embodiments, a compound of structural Formula (IXa) is provided:

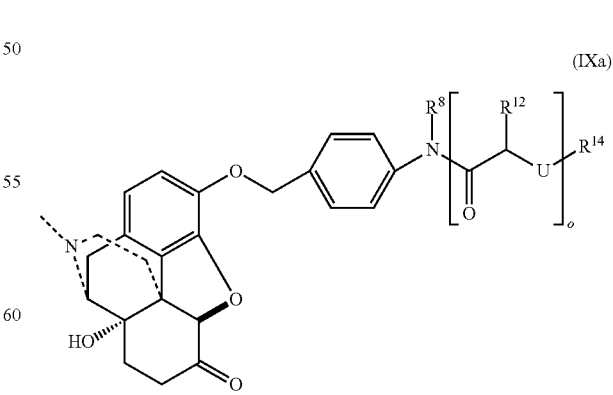
(IXa)

or salts, hydrates or solvates thereof $R^8$ is hydrogen or methyl, $R^{12}$ is an amino acid side chain, $R^{14}$ is hydrogen, acyl, or —$CO_2$-t-butyl, and o is an integer from 1 to 5.

In still other embodiments, a compound of structural Formula (IXb) is provided:

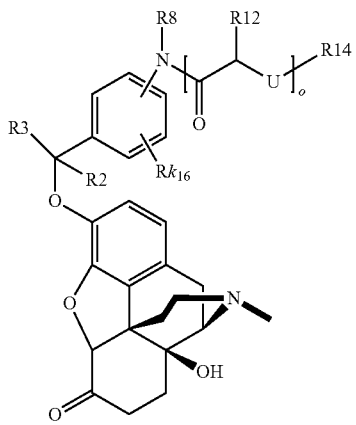
(IXb)

or salts, hydrates or solvates thereof, wherein $R^2$ and $R^3$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl; $R^8$ is hydrogen or methyl, $R^{12}$ is an amino acid side chain, $R^{14}$ is hydrogen, acyl, or $-CO_2$-t-butyl, o is an integer from 1 to 5, $R_k^{16}$ are each independently selected from the group consisting of one or more of $-F$, $-Cl$, $-Br$, $-I$, $-R^4$, $-O^-$, $-OR^4$, $-SR^4$, $-S^-$, $-NR^4R^5$, $-CF_3$, $-CN$, $-OCN$, $-SCN$, $-NO$, $-NO_2$, $-N_3$, $-S(O)_2O^-$, $-S(O)_2OH$, $-S(O)_2R^4$, $-OS(O_2)O^-$, $-OS(O)_2R^4$, $-P(O)(O^-)_2$, $-P(O)(OR^4)(O^-)$, $-OP(O)(OR^4)(OR^5)$, $-C(O)R^4$, $-C(S)R^4$, $-C(O)OR^4$, $-C(O)NR^4R^5$, $-C(O)O^-$, $-C(S)OR^4$, $-NR^6C(O)NR^4R^5$, $-NR^6C(S)NR^4R^5$, $-NR^7C(NR^6)NR^5R^4$ or $-C(NR^6)NR^5R^4$, and k is 0, 1, 2, 3, or 4, provided that substituent $NR^8$ is oriented para or ortho to $CR^2R^3$.

In some embodiments, a compound of structural Formula (X) is provided:

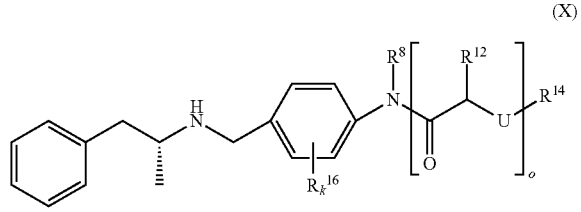
(X)

or salts, hydrates or solvates thereof $R^8$ is hydrogen or methyl, $R^{12}$ is an amino acid side chain, $R^{14}$ is hydrogen, acyl, or $-CO_2$-t-butyl, o is an integer from 1 to 5, $R_k^{16}$ are each independently selected from the group consisting of one or more of $-F$, $-Cl$, $-Br$, $-I$, $-R^4$, $-O^-$, $-OR^4$, $-SR^4$, $-S^-$, $-NR^4R^5$, $-CF_3$, $-CN$, $-OCN$, $-SCN$, $-NO$, $-NO_2$, $-N_3$, $-S(O)_2O^-$, $-S(O)_2OH$, $-S(O)_2R^4$, $-OS(O_2)O^-$, $-OS(O)_2R^4$, $-P(O)(O^-)_2$, $-P(O)(OR^4)(O^-)$, $-OP(O)(OR^4)(OR^5)$, $-C(O)R^4$, $-C(S)R^4$, $-C(O)OR^4$, $-C(O)NR^4R^5$, $-C(O)O^-$, $-C(S)OR^4$, $-NR^6C(O)NR^4R^5$, $-NR^6C(S)NR^4R^5$, $-NR^7C(NR^6)NR^5R^4$ or $-C(NR^6)NR^5R^4$, and k is 0, 1, 2, 3, or 4.

n some embodiments, a compound of structural Formula (Xa) is provided:

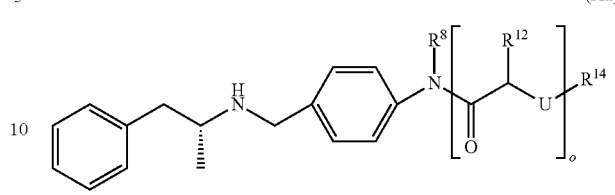
(Xa)

or salts, hydrates or solvates thereof $R^8$ is hydrogen or methyl, $R^{12}$ is an amino acid side chain, $R^{14}$ is hydrogen, acyl, or $-CO_2$-t-butyl, and o is an integer from 1 to 5.

In still other embodiments, a compound of structural Formula (Xb) is provided:

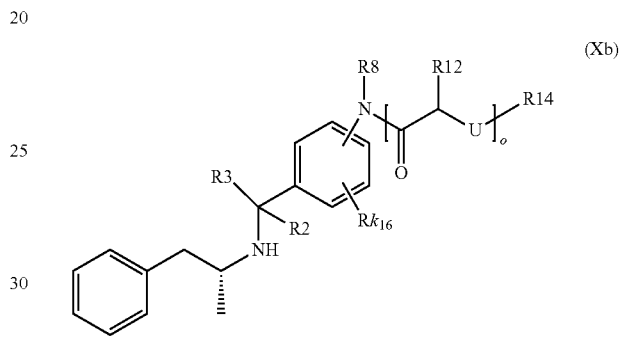
(Xb)

or salts, hydrates or solvates thereof, wherein $R^2$ and $R^3$ are independently hydrogen, alkyl, 5 substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl; $R^8$ is hydrogen or methyl, $R^{12}$ is an amino acid side chain, $R^{14}$ is hydrogen, acyl, or $-CO2$-t-butyl, o is an integer from 1 to 5, $R_k^{16}$ are each independently selected from the group consisting of one or more of $-F$, $-Cl$, $-Br$, $-I$, $-R^4$, $-O^-$, $-OR^4$, $-SR^4$, $-S^-$, $-NR^4R^5$, $-CF_3$, $-CN$, $-OCN$, $-SCN$, $-NO$, $-NO_2$, $-N_3$, $-S(O)_2O^-$, $-S(O)_2OH$, $-S(O)_2R^4$, $-OS(O_2)O^-$, $-OS(O)_2R^4$, $-P(O)(O^-)_2$, $-P(O)(OR^4)(O^-)$, $-OP(O)(OR^4)(OR^5)$, $-C(O)R^4$, $-C(S)R^4$, $-C(O)OR^4$, $-C(O)NR^4R^5$, $-C(O)O^-$, $-C(S)OR^4$, $-NR^6C(O)NR^4R^5$, $-NR^6C(S)NR^4R^5$, $-NR^7C(NR^6)NR^5R^4$ or $-C(NR^6)NR^5R^4$, and k is 0, 1, 2, 3, or 4, provided that substituent $NR^8$ is oriented para or ortho to $CR^2R^3$.

In other embodiments, a compound of structural Formula (XI) is provided:

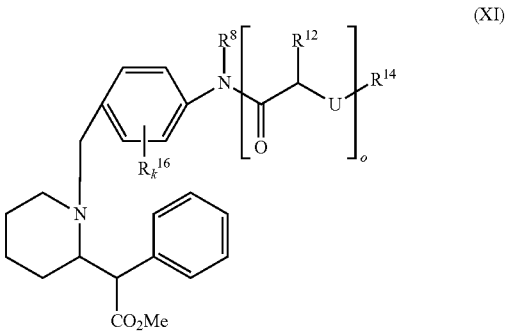
(XI)

or salts, hydrates or solvates thereof $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ or —$C(NR^6)NR^5R^4$, and k is 0, 1, 2, 3, or 4.

In other embodiments, a compound of structural Formula (XIa) is provided:

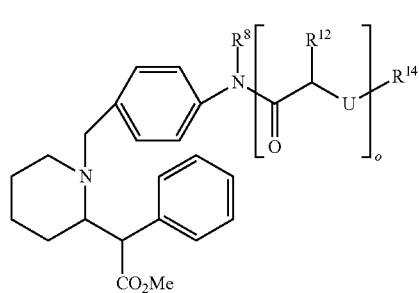

or salts, hydrates or solvates thereof $R^8$ is hydrogen or methyl, $R^{12}$ is an amino acid side chain, $R^{14}$ is hydrogen, acyl, or —$CO_2$-t-butyl, and o is an integer from 1 to 5.

In still other embodiments, a compound of structural Formula (XIb) is provided:

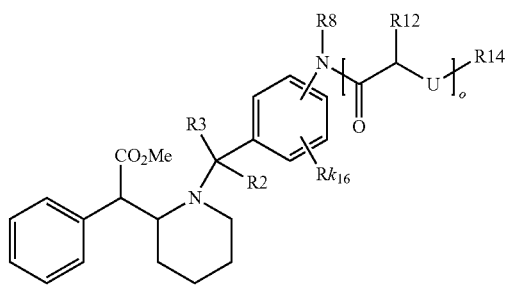

or salts, hydrates or solvates thereof, wherein $R^2$ and $R^3$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl; $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ or —$C(NR^6)NR^5R^4$, and k is 0, 1, 2, 3, or 4, provided that substituent $NR^8$ is oriented para or ortho to $CR^2R^3$.

In still other embodiments, a compound of structural Formula (XII) is provided:

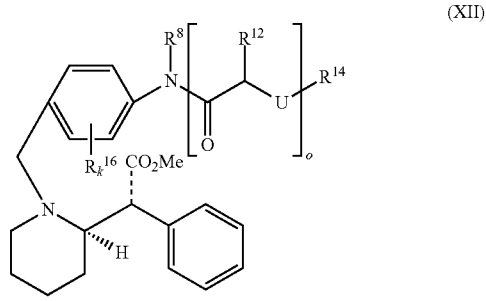

or salts, hydrates or solvates thereof $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ or —$C(NR^6)NR^5R^4$, and k is 0, 1, 2, 3, or 4.

In still other embodiments, a compound of structural Formula (XIIa) is provided:

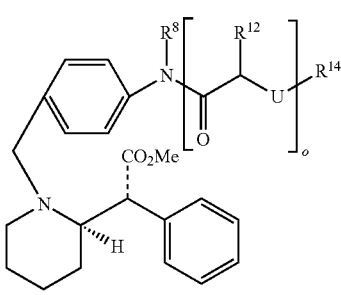

or salts, hydrates or solvates thereof $R^8$ is hydrogen or methyl, $R^{12}$ is an amino acid side chain, $R^{14}$ is hydrogen, acyl, or —$CO_2$-t-butyl, and o is an integer from 1 to 5.

In still other embodiments, a compound of structural Formula (XIIb) is provided:

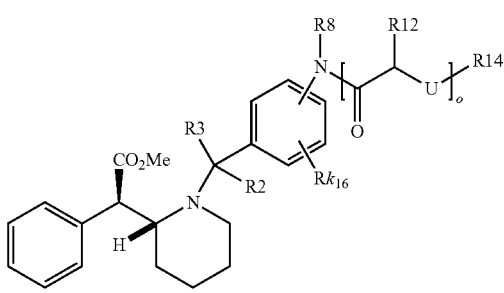

or salts, hydrates or solvates thereof, wherein $R^2$ and $R^3$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl; $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ or —$C(NR^6)NR^5R^4$, and k is 0, 1, 2, 3, or 4, provided that substituent $NR^8$ is oriented para or ortho to $CR^2R^3$.

In some embodiments, the present invention provides methods for forming an active agent (i.e., where XH has been generated). In some embodiments, a prodrug of Formula (I) and/or Formula (II) is contacted with an enzyme including, but not limited to, pepsin, trypsin, chymotrypsin, colipase, elastase, aminopeptidase N, aminopeptidase A, dipeptidylaminopeptidase IV, tripeptidase, enteropeptidase, dipeptidase, or tripeptidase or combinations thereof.

While not wishing to be bound by theory, a prodrug of Formula (I) and/or Formula (II) may be enzymatically hydrolyzed by peptidases in the body to provide the free active agent (i.e., X-H). In some embodiments, the enzyme is a digestive enzyme such as, for example, pepsin, trypsin, chymotrypsin, colipase, elastase, aminopeptidase N, aminopeptidase A, dipeptidylaminopeptidase IV, tripeptidase, enteropeptidase or combinations thereof.

In some embodiments, the prodrugs of Formula (I) and/or (II) prevent inadvertent and/or intentional abuse of the parent drug. While not wishing to be bound by theory, it is contemplated that many of the prodrugs of Formula (I) may provide controlled release rather than immediate release when administered, for example, via injection, intranasally, sublingually, etc.

In other embodiments, the prodrugs of Formula (I) and/or (II) prevent overdosing of the parent drug. While not wishing to be bound by theory, it is contemplated that many of the prodrugs of Formula (I) may convert incompletely or at sufficiently slow rate to the parent drug.

4.3 Methods of Synthesis

The compounds described herein may be obtained via the synthetic methods illustrated in Schemes 1-2. The promoieties described herein, may be prepared and attached to active agents by established procedures known to those of skill in the art (See e.g., Green et al., "Protective Groups in Organic Chemistry", (Wiley, $2^{nd}$ ed. 1991); Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995, Bodanzsky, "Principles of Peptide Synthesis," Springer Verlag, 1984; Bodanzsky, "Practice of Peptide Synthesis," Springer Verlag, 1984).

Other methods for synthesis of the prodrugs described herein will be readily apparent to the skilled artisan and may be used to synthesize the compounds described herein. Accordingly, the methods presented in the Schemes herein are illustrative rather than comprehensive.

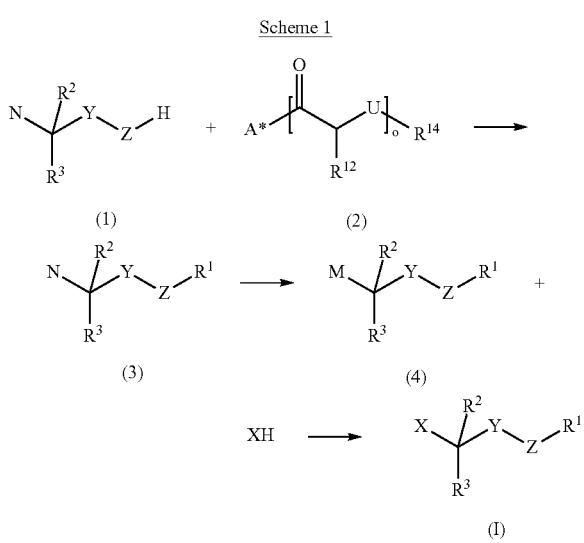

Scheme 1

As illustrated in Scheme 1, supra, one method of synthesis of a prodrug of Formula (I). Here, compound (1) where N is a capable of being converted to a leaving group, and $R^2$, $R^3$, Y and Z are as previously defined and compound (2) where A, $R^{12}$, $R^{14}$, U and o are as previously defined are reacted under standard conditions to provide functionalized derivative. Compound (3) is converted to compound (4) under standard conditions then now reacted with active agent XH under conventional conditions to provide a prodrug of Formula (I). The active agent XH may be purchased from commercial sources or synthesized using known procedures.

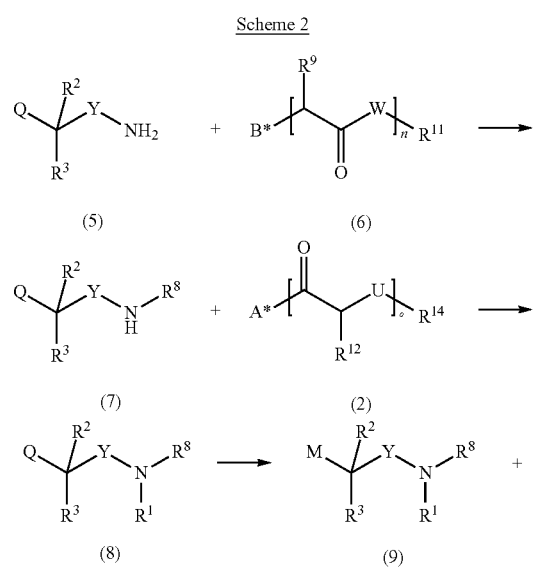

Scheme 2

-continued

XH ⟶ 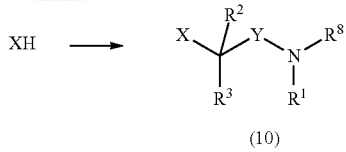

(10)

Shown above in Scheme 2 is a synthetic strategy for synthesizing compound (10) where Z is $NR^1R^8$. Here, compound (5) where Q is a capable of being converted to a leaving group, and $R^2$, $R^3$, and Y are as previously defined and compound (6) where B, $R^{12}$, $R^{11}$, W and n are as previously defined are reacted under standard conditions to form compound (7). Compound (7) may be reacted under conventional conditions with compound (2) to yield compound (8). Compound (8) is converted to compound (9) under standard conditions then now reacted with active agent XH under conventional conditions to provide a prodrug of compound (10).

4.4 Therapeutic Methods of Use

In general, the prodrugs disclosed herein may be used to treat and/or prevent the same disease(s) and/or conditions as the parent drug which are well known in the art (see, e.g., Physicians Desk Reference, 59$^{th}$ Edition and the Merck Index, 13$^{th}$ Edition). For example, the prodrug of an angiotensin converting enzyme inhibitor could be used, inter alia, to treat or prevent hypertension.

The invention further provides methods for altering actives agents in a manner that decreases their potential for abuse or overdose. Methods of the invention provide various ways to regulate pharmaceutical dosage through covalent attachment of active agents to different chemical moieties described herein.

Another embodiment provides a method of safely delivering an active agent comprising providing a therapeutically effective amount of a compound of structural Formula (I) or (II) which reduces the rate of absorption of active agent as compared to delivering the active agent alone.

Another embodiment provides a method of reducing the toxicity of an active agent comprising providing a patient with a compound of structural Formula (I) or (II). Another embodiment provides a method of reducing toxicity or an active agent comprising providing a patient with a compound of structural Formula (I) or (II), wherein the compound provides a serum release curve which does not increase above the active agents toxicity level when given at doses exceeding those within the therapeutic range for the active agent alone. Another embodiment provides a method of reducing bioavailability of an active agent comprising providing a compound of structural Formula (I) or (II), wherein the compound maintains a steady-state serum release curve which provides a therapeutically effective bioavailability but prevents spiking or increase blood serum concentrations compared to the active agent alone when given at doses exceeding those within the therapeutic range for the active agent.

Another embodiment of the invention is a method for reducing, deterring, or preventing abuse of an active agent comprising providing, administering, or prescribing a compound of structural Formula (I) or (II) to a human in need thereof, wherein the pharmacological activity of compound is decreased when the compound is used in a manner inconsistent with the manufacturer's instructions.

Another embodiment of the invention is a method for reducing, deterring, or preventing abuse of an active agent comprising consuming a compound of structural Formula (I) or (II), such that the pharmacological activity of active agent is substantially decreased when the compound is used in a manner inconsistent with the manufacturer's instructions.

Another embodiment of the invention is a method of reducing, deterring, or preventing an overdose of active agent comprising providing, administering, or prescribing a compound of structural Formula (I) or (II), to a human in need thereof, wherein said compound decreases the potential of overdose from the active agent.

Another embodiment of the invention is a method for reducing, deterring, or preventing the euphoric effect of active agent comprising providing, administering, or prescribing to a human in need thereof, a compound of structural Formula (I) or (II), wherein the pharmacological activity of active agent is decreased when the compound is used in a manner inconsistent with the manufacturer's instructions.

In a specific embodiment, an opioid prodrug and/or pharmaceutical compositions thereof is administered to a subject to treat and/or prevent pain. The type of pain which may treated by methods disclosed herein include, but are not limited to, acute pain, chronic pain, neuropathic pain, acute traumatic pain, arthritic pain, osteoarthritic pain, rheumatoid arthritic pain, musculoskeletal pain, post-dental surgical pain, dental pain, myofascial pain, cancer pain, visceral pain, diabetic pain, muscular pain, post-herpetic neuralgic pain, chronic pelvic pain, endometriosis pain, pelvic inflammatory pain and child birth related pain. Acute pain includes, but is not limited to, acute traumatic pain or post-surgical pain. Chronic pain includes, but is not limited to, neuropathic pain, arthritic pain, osteoarthritic pain, rheumatoid arthritic pain, musculoskeletal pain, dental pain, myofascial pain, cancer pain, diabetic pain, visceral pain, muscular pain, post-herpetic neuralgic pain, chronic pelvic pain, endometriosis pain, pelvic inflammatory pain and back pain. In some embodiments, when the subject is a human female, chronic pain includes, in particular, chronic pelvic pain, endometriosis pain, pelvic inflammatory pain and child-birth related pain.

In a specific embodiment, an amphetamine, or derivative thereof, prodrug and/or pharmaceutical compositions thereof is administered to a subject to treat and/or prevent attention deficit hyperactivity disorder, narcolepsy or obesity. For instance, one embodiment of the invention comprises a method of treating attention deficit hyperactivity disorder (ADHD) comprising administering to a patient a compound of structural Formula (I) or (II) wherein X is an amphetamine. Another embodiment of the invention provides a method of treating narcolepsy comprising administering to a patient compounds of the invention. Another embodiment of the invention provides a method of treating obesity comprising administering to a patient compounds of the invention.

4.5 Pharmaceutical Compositions

The pharmaceutical compositions disclosed herein comprise a prodrug disclosed herein with a suitable amount of a pharmaceutically acceptable vehicle, so as to provide a form for proper administration to a subject.

Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compositions and compounds disclosed herein into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained—Release formulations, suppositories, emulsions, aerosols, sprays, suspensions or any other form suitable for use known to the skilled artisan. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19$^{th}$ Edition, 1995).

Pharmaceutical compositions for oral delivery may be in the form of tablets, lozenges, aqueous or oily suspensions, granules, powders, emulsions, capsules, syrups, slurries, suspensions or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, sucrose, sorbitol, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), granulating agents, binding agents and disintegrating agents such as the cross-linked polyvinylpyrrolidone, agar, or alginic acid or a salt thereof such as sodium alginate etc.

In some embodiments, pharmaceutical compositions are in the form of lozenges or lollipops where dissolution and release of the active ingredients occurs in the oral cavity, generally through the oral mucosa. For these embodiments, buffering agents may also be used to provide an optimum environment for delivery of the agents or compositions. Additional components may include, for example, sweeteners, binders, diluents, disintegrating agents, lubricating agents, etc.

In still other embodiments, the pharmaceutical composition is a dissolving sublingual tablet, where dissolution and release of the active ingredients occurs under the tongue, and the compositions and/or compounds disclosed herein are absorbed through the oral mucosa. In these embodiments, buffer agents may also be used to provide an optimum environment for delivery of each of the agents. Additional components may include, for example, sweeteners, binders, diluents, disintegrating agents, etc.

The methods that involve oral administration of compounds disclosed herein of can also be practiced with a number of different dosage forms, which provide sustained release.

In some embodiments, the dosage form is comprised of beads that on dissolution or difflusion release compositions and/or compounds disclosed herein over an extended period of hours, preferably, over a period of at least 6 hours, more preferably, over a period of at least 8 hours and even more preferably, over a period of at least 12 hours and most preferably, over a period of at least 24 hours. The beads may have a central composition or core comprising compounds disclosed herein and pharmaceutically acceptable vehicles, including optional lubricants, antioxidants and buffers. The beads may be medical preparations with a diameter of about 1 to about 2 mm. Individual beads may comprise doses of the compounds disclosed herein. The beads, in some embodiments, are formed of non-cross-linked materials to enhance their discharge from the gastrointestinal tract. The beads may be coated with a release rate-controlling polymer that gives a timed-release profile.

The time-release beads may be manufactured into a tablet for therapeutically effective administration. The beads can be made into matrix tablets by direct compression of a plurality of beads coated with, for example, an acrylic resin and blended with excipients such as hydroxypropylmethyl cellulose. The manufacture of beads has been disclosed in the art (Lu, Int. J Pharm. 1994, 112, 117-124; Pharmaceutical Sciences by Remington, 14$^{th}$ ed, pp 1626-1628 (1970); Fincher, J Pharm. Sci. 1968, 57, 1825-1835; Benedikt, U.S. Pat. No. 4,083,949) as has the manufacture of tablets (Pharmaceutical Sciences, by Remington, 17$^{th}$ Ed, Ch. 90, pp 1603-1625 (1985).

In other embodiments, an oral sustained release pump may be used (Langer, supra; Sefton, 1987, CRC Crit Ref Biomed. Eng. 14:201; Saudek et al., 1989, N. Engl. J Med. 321:574).

In still other embodiments, polymeric materials can be used (See "Medical Applications of Controlled Release," Langer and Wise (eds.), CRC Press., Boca Raton, Fla. (1974); "Controlled Drug Bioavailability," Drug Product Design and Performance, Smolen and Ball (eds.), Wiley, New York (1984); Langer et al., 1983, J Macromol. Sci. Rev. Macromol Chem. 23:61; Levy et al., 1985, Science 228: 190; During et al., 1989, Ann. Neurol. 25:351; Howard et al., 1989, J. Neurosurg. 71:105). In some embodiments, polymeric materials are used for oral sustained release delivery. Such polymers include, for example, sodium carboxymethylcellulose, hydroxypropylcellulose, hydroxypropylmethylcellulose and hydroxyethylcellulose. Other cellulose ethers have been described (Alderman, Int. J. Pharm. Tech. & Prod. Mfr. 1984, 5(3) 1-9). Factors affecting drug release are well known to the skilled artisan and have been described in the art (Bamba et al., Int. J. Pharm. 1979, 2, 307).

In still other embodiments, enteric-coated preparations can be used for oral sustained release administration. Coating materials include, for example, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In yet other embodiments, drug-releasing lipid matrices can be used for oral sustained release administration. For example, solid microparticles of compositions and/or compounds disclosed herein may be coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700. The lipid-coated particles can optionally be compressed to form a tablet. Another controlled release lipid-based matrix material which is suitable for sustained release oral administration comprises polyglycolized glycerides as disclosed in Roussin et al., U.S. Pat. No. 6,171,615.

In yet other embodiments, waxes can be used for oral sustained release administration. Examples of suitable sustained releasing waxes are disclosed in Cain et al., U.S. Pat. No. 3,402,240 (camauba wax, candedilla wax, esparto wax and ouricury wax); Shtohryn et al., U.S. Pat. No. 4,820,523 (hydrogenated vegetable oil, bees wax, caranuba wax, paraffin, candelillia, ozokerite and mixtures thereof); and Walters, U.S. Pat. No. 4,421,736 (mixture of paraffin and castor wax).

In still other embodiments, osmotic delivery systems are used for oral sustained release administration (Verma et al., *Drug Dev. Ind. Pharm.* 2000, 26:695-708). In some embodiments, OROS® systems made by Alza Corporation, Mountain View, Calif. are used for oral sustained release delivery devices (Theeuwes et al., U.S. Pat. No. 3,845,770; Theeuwes et al., U.S. Pat. No. 3,916,899).

In yet other embodiments, a controlled-release system can be placed in proximity of the target of the compositions and/or compounds disclosed herein thus requiring only a fraction of the systemic dose (See, e.g., Goodson, in "Medical Applications of Controlled Release," supra, vol. 2, pp. 115-138 (1984)). Other controlled-release systems are discussed in Langer, 1990, *Science* 249:1527-1533 may also be used.

In still other embodiments, the dosage form comprises compounds disclosed herein coated on a polymer substrate. The polymer can be an erodible, or a non-erodible polymer. The coated substrate may be folded onto itself to provide a bilayer polymer drug dosage form. For example, compounds disclosed herein can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense the compounds over a sustained release period. Representative biodegradable polymers comprise a member selected from the group consisting of biodegradable poly(amides), poly(amino acids), poly(esters), poly (lactic acid), poly(glycolic acid), poly(carbohydrate), poly (orthoester), poly(orthocarbonate), poly(acetyl), poly (anhydrides), biodegradable poly(dihydropyrans), and poly (dioxinones) which are known in the art (Rosoff, *Controlled Release of Drugs*, Chap. 2, pp. 53-95 (1989); Heller et al., U.S. Pat. No. 3,811,444; Michaels, U.S. Pat. No. 3,962,414; Capozza, U.S. Pat. No. 4,066,747; Schmitt, U.S. Pat. No. 4,070,347; Choi et al., U.S. Pat. No. 4,079,038; Choi et al., U.S. Pat. No. 4,093,709).

In other embodiments, the dosage form comprises compounds disclosed herein loaded into a polymer that releases the drug(s) by diffusion through a polymer, or by flux through pores or by rupture of a polymer matrix. The drug delivery polymeric dosage form comprises a concentration of 10 mg to 2500 mg homogenously contained in or on a polymer. The dosage form comprises at least one exposed surface at the beginning of dose delivery. The non-exposed surface, when present, is coated with a pharmaceutically acceptable material impermeable to the passage of the drug(s). The dosage form may be manufactured by procedures known in the art. An example of providing a dosage form comprises blending a pharmaceutically acceptable carrier like polyethylene glycol, with a known dose of compositions and/or compounds disclosed herein at an elevated temperature, (e.g., 37° C.), and adding it to a silastic medical grade elastomer with a cross-linking agent, for example, octanoate, followed by casting in a mold. The step is repeated for each optional successive layer. The system is allowed to set for about 1 hour, to provide the dosage form. Representative polymers for manufacturing the dosage form comprise a member selected from the group consisting of olefin, and vinyl polymers, addition polymers, condensation polymers, carbohydrate polymers, and silicone polymers as represented by polyethylene, polypropylene, polyvinyl acetate, polymethylacrylate, polyisobutylmethacrylate, poly alginate, polyamide and polysilicone. The polymers and procedures for manufacturing them have been described in the art (Coleman et al., *Polymers* 1990, 31, 1187-1231; Roerdink et al., *Drug Carrier Systems* 1989, 9, 57-10; Leong et al., *Adv. Drug Delivery Rev.* 1987, 1, 199-233; Roff et al., *Handbook of Common Polymers* 1971, CRC Press; Chien et al., U.S. Pat. No. 3,992,518).

In other embodiments, the dosage form comprises a plurality of tiny pills. The tiny time-release pills provide a number of individual doses for providing various time doses for achieving a sustained-release drug delivery profile over an extended period of time up to 24 hours. The matrix comprises a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, grum tragacanth, locust bean gum, pectin, amylopectin, gelatin, and a hydrophilic colloid. The hydrophilic matrix comprises a plurality of 4 to 50 tiny pills, each tiny pill comprise a dose population of from 10 ng, 0.5 mg, 1 mg, 1.2 mg, 1.4 mg, 1.6 mg, 5.0 mg, etc. The tiny pills comprise a release rate-controlling wall of 0.001 mm up to 10 mm thickness to provide for the timed release of drug(s). Representative wall forming materials include a triglyceryl ester selected from the group consisting of glyceryl tristearate, glyceryl monostearate, glyceryl dipalmitate, glyceryl laureate, glyceryl didecenoate and glyceryl tridenoate. Other wall forming materials comprise polyvinyl acetate, phthalate, methylcellulose phthalate and microporous olefins. Procedures for manufacturing tiny pills are disclosed in Urquhart et al., U.S. Pat. No. 4,434,153; Urquhart et al., U.S. Pat. No. 4,721,613; Theeuwes, U.S. Pat. No. 4,853,229; Barry, U.S. Pat. No. 2,996,431; Neville, U.S. Pat. No. 3,139,383; Mehta, U.S. Pat. No. 4,752,470.

In other embodiments, the dosage form comprises an osmotic dosage form, which comprises a semipermeable wall that surrounds a therapeutic composition comprising compounds disclosed herein. In use within a subject, the osmotic dosage form comprising a homogenous composition, imbibes fluid through the semipermeable wall into the dosage form in response to the concentration gradient across the semipermeable wall. The therapeutic composition in the dosage form develops osmotic pressure differential that causes the therapeutic composition to be administered through an exit from the dosage form over a prolonged period of time up to 24 hours (or even in some cases up to 30 hours) to provide controlled and sustained release. These delivery platforms can provide an essentially zero order delivery profile as opposed to the spiked profiles of immediate release formulations.

In other embodiments, the dosage form comprises another osmotic dosage form comprising a wall surrounding a compartment, the wall comprising a semipermeable polymeric composition permeable to the passage of fluid and substantially impermeable to the passage of compounds disclosed herein present in the compartment, a drug-containing layer composition in the compartment, a hydrogel push layer composition in the compartment comprising an osmotic formulation for imbibing and absorbing fluid for expanding in size for pushing the drug composition layer from the dosage form, and at least one passageway in the wall for releasing the composition. The method delivers compounds disclosed herein by imbibing fluid through the semipermeable wall at a fluid imbibing rate determined by the permeability of the semipermeable wall and the osmotic pressure across the semipermeable wall causing the push layer to expand, thereby delivering the compounds disclosed herein from the dosage form through the exit passageway to a subject over a prolonged period of time (up to 24 or even 30 hours). The hydrogel layer composition may comprise 10 mg to 1000 mg of a hydrogel such as a member selected from the group consisting of a polyalkylene oxide of 1,000,000 to 8,000,000 weight-average molecular weight which are selected from the group consisting of a polyethylene oxide of 1,000,000 weight-average molecular weight, a polyethylene oxide of 2,000,000 weight-average molecular weight, a polyethylene oxide of 4,000,000 weight-average molecular weight, a polyethylene oxide of 5,000,000 weight-average molecular weight, a polyethylene oxide of 7,000,000 weight-average molecular weight and a polypropylene oxide of the 1,000,000 to 8,000,000 weight-average molecular weight; or 10 mg to 1000 mg of an alkali carboxymethylcellulose of 10,000 to 6,000,000 weight-average molecular weight, such as sodium carboxymethylcellulose or potassium carboxymethylcellulose. The hydrogel expansion layer comprises 0.0 mg to 350 mg, in present manufacture; 0.1 mg to 250 mg of a hydroxyalkylcellulose of 7,500 to 4,500,000 weight-average molecular weight (e.g., hydroxymethylcellulose, hydroxyethylcellulose, hydroxypropylcellulose, hydroxybutylcellulose or hydroxypentylcellulose) in present manufacture; 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, in a present manufacture, 0.1 mg to 30 mg of a hydroxypropylalkylcellulose of 9,000 to 225,000 weight-average molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylated hydroxyquinone, butylhydroxyanisole, hydroxycoumarin, butylated hydroxytoluene, cephalm, ethyl gallate, propyl gallate, octyl gallate, lauryl gallate, propylhydroxybenzoate, trihydroxybutyrophenone, dimethylphenol, dibutylphenol, vitamin E, lecithin and ethanolamine; and 0.0 mg to 7 mg of a lubricant selected from the group consisting of calcium stearate, magnesium stearate, zinc stearate, magnesium oleate, calcium palmitate, sodium suberate, potassium laurate, salts of fatty acids, salts of alicyclic acids, salts of aromatic acids, stearic acid, oleic acid, palmitic acid, a mixture of a salt of a fatty, alicyclic or aromatic acid and a fatty, alicyclic or aromatic acid.

In the osmotic dosage forms, the semipermeable wall comprises a composition that is permeable to the passage of fluid and impermeable to the passage of compounds disclosed herein. The wall is non-toxic and comprises a polymer selected from the group consisting of a cellulose acylate, cellulose diacylate, cellulose triacylate, cellulose acetate, cellulose diacetate and cellulose triacetate. The wall comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether selected from the group consisting of hydroxypropylcellulose or a hydroxypropylalkylcellulose such as hydroxypropylmethylcellulose. The total weight percent of all components comprising the wall is equal to 100 wt %. The internal compartment comprises the drug-Containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of compounds disclosed herein to a subject over time. The dosage form comprises a passageway in the wall that connects the exterior of the dosage form with the internal compartment. The osmotic powered dosage form can be made to deliver drug from the dosage form to the subject at a 0-order rate of release over a period of up to about 24 hours.

The expression "passageway" as used herein comprises means and methods suitable for the metered release of the compounds disclosed herein from the compartment of the dosage form. The exit means comprises at least one passageway, including orifice, bore, aperture, pore, porous element, hollow fiber, capillary tube, channel, porous overlay, or porous element that provides for the osmotic controlled release of the compounds disclosed herein. The passageway includes a material that erodes or is leached from the wall in a fluid environment of use to produce at least one controlled-release dimensioned passageway. Representative materials suitable for forming a passageway, or a multiplicity of passageways comprise a leachable poly(glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of compositions and/or drugs from the dosage form. The dosage form can be constructed with one or more passageways is spaced apart relationship on a single surface or on more than one surface of the wall. The expression "fluid environment" denotes an aqueous or biological fluid as in a human patient, including the gastrointestinal tract. Passageways and equipment for forming passageways are disclosed in Theeuwes et al., U.S. Pat. No. 3,845,770; Theeuwes et al., U.S. Pat. No. 3,916,899; Saunders et aL., U.S. Pat. No. 4,063,064; Theeuwes et al., U.S. Pat. No. 4,088,864 and Ayer et al., U.S. Pat. No. 4,816,263. Passageways formed by leaching are disclosed in Ayer et al., U.S. Pat. No. 4,200,098 and Ayer et al., U.S. Pat. No. 4,285,987.

In order to decrease dosing frequency and augment the convenience to the subject and increase subject compliance, the sustained release oral dosage form (regardless of the specific form of the sustained release dosage form) preferably, provides therapeutic concentrations of the compounds disclosed herein in the patient's blood over a period of at least about 6 hours, more preferably, over a period of at least about 8 hours, even preferably, over a period of at least about 12 hours and most preferably, over a period of at least 24 hours.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

Liquid drug formulations suitable for use with nebulizers and liquid spray devices and EHD aerosol devices will typically include compounds disclosed herein with a pharmaceutically acceptable carrier such as, for example, a liquid (e.g., alcohol, water, polyethylene glycol or a perfluorocarbon). Optionally, another material may be added to alter the aerosol properties of the solution or suspension of compositions and/or compounds disclosed herein. In some embodiments, this material is liquid such as an alcohol, glycol, polyglycol or a fatty acid. Other methods of formulating liquid drug solutions or suspension suitable for use in aerosol devices are known to those of skill in the art (Biesalski, U.S. Pat. No. 5,112,598; Biesalski, U.S. Pat. No. 5,556,611)

For topical administration a compound disclosed herein may be formulated as solutions, gels, ointments, creams, suspensions, etc. as are well-known in the art.

For buccal administration, the compounds disclosed herein may take the form of tablets, lozenges, lollipops, etc. formulated in a conventional manner.

Compounds disclosed herein may also be formulated in rectal or vaginal compositions such as suppositories or retention enemas, e.g., containing conventional suppository bases such as cocoa butter or other glycerides.

Systemic formulations include those designed for administration by injection, e.g., subcutaneous, intravenous, intramuscular, intrathecal or intraperitoneal injection, as well as those designed for transdernal, transmucosal, oral or pulmonary administration. Systemic formulations may be made in combination with a further active agent that improves mucociliary clearance of airway mucus or reduces mucous viscosity. These active agents include but are not limited to sodium channel blockers, antibiotics, N-acetyl cysteine, homocysteine and phospholipids.

For injection, compounds disclosed herein may be formulated in aqueous solutions, such as physiologically compatible buffers such as Hanks' solution, Ringer's solution, physiological saline buffer or in association with a surface-active agent (or wetting agent or surfactant) or in the form of an emulsion (as a water-in-oil or oil-in-water emulsion). Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent may comprise between 0.05 and 5% surface-active agent or between 0.1 and 2.5% surface-active agent. The solution may contain formulatory agents such as suspending, stabilizing and/or dispersing agents. Alternatively, compounds disclosed herein may be in powder form for constitution with a suitable vehicle, e.g., sterile pyrogen-free water, before use.

Suitable emulsions may be prepared using commercially available fat emulsions. The combination (or single components) may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. In some embodiments, EDTA is added as a preservative.

In addition to the formulations described previously, compounds disclosed herein may also be formulated as a depot preparation. Such long acting formulations may be administered by implantation (for example, subcutaneously or intramuscularly) or by intramuscular injection. Thus, for example, compounds disclosed herein may be formulated with suitable polymeric or hydrophobic materials (for example, as an emulsion in an acceptable oil) or ion exchange resins, or as sparingly soluble derivatives, for example, as a sparingly soluble salt.

4.6 Therapeutic/Prophylactic Administration and Doses

When used to treat and/or prevent diseases the prodrugs disclosed herein and/or pharmaceutical compositions thereof may be administered alone or in combination with other pharmaceutical agents including compounds disclosed herein and/or pharmaceutical compositions thereof. The compounds disclosed herein may be administered or applied per se or as pharmaceutical compositions. The specific pharmaceutical composition depends on the desired mode of administration, as is well known to the skilled artisan.

Compounds disclosed herein and/or pharmaceutical compositions thereof may be administered to a subject by intravenous bolus injection, continuous intravenous infusion, oral tablet, oral capsule, oral solution, intramuscular injection, subcutaneous injection, transdermal absorption, buccal absorption, intranasal absorption, inhalation, sublingual, intracerebrally, intravaginally, rectally, topically, particularly to the ears, nose, eyes, or skin or any other convenient method known to those of skill in the art. In some embodiments, compounds disclosed herein and/or pharmaceutical compositions thereof are delivered via sustained release dosage forms, including oral sustained release dosage forms. Administration can be systemic or local. Various delivery systems are known, (e.g., encapsulation in liposomes, microparticles, microcapsules, capsules, "patient controlled analgesia" drug delivery systems, etc.) that can be used to deliver compounds disclosed herein and/or pharmaceutical compositions thereof.

Compounds disclosed herein and/or pharmaceutical compositions thereof may also be administered directly to the lung by inhalation. For administration by inhalation, the compounds disclosed herein and/or pharmaceutical compositions thereof may be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas may be used to deliver the compounds disclosed herein and/or pharmaceutical compositions thereof.

Alternatively, a Dry Powder Inhaler ("DPI") device may be used to administer compounds disclosed herein and/or pharmaceutical compositions thereof (See, e.g., Raleigh et al., *Proc. Amer. Assoc. Cancer Research Annual Meeting*, 1999, 40, 397). DPI devices typically use a mechanism such as a burst of gas to create a cloud of dry powder inside a container, which may then be inhaled by the patient. A popular variation is the multiple dose DPI ("MDDPI") system, which allows for the delivery of more than one therapeutic dose. For example, capsules and cartridges of gelatin for use in an inhaler or insufflator may be formulated containing a powder mix of the compositions and/or compounds disclosed herein and a suitable powder base such as lactose or starch for these systems.

Another type of device that may be used to deliver the compounds disclosed herein and/or pharmaceutical compositions thereof is a liquid spray device supplied, for example, by Aradigm Corporation, Hayward, Calif. Liquid spray systems use extremely small nozzle holes to aerosolize liquid drug formulations that may then be directly inhaled.

In some embodiments, a nebulizer device is used to deliver compounds and/or pharmaceutical compositions thereof disclosed herein. Nebulizers create aerosols from liquid drug formulations by using, for example, ultrasonic energy to form fine particles that may be readily inhaled (e.g., Verschoyle et al., *British J. Cancer,* 1999, 80, Suppl. 2, 96; Armer et al., U.S. Pat. No. 5,954,047; van der Linden et al., U.S. Pat. No. 5,950,619; van der Linden et al., U.S. Pat. No. 5,970,974).

In still other embodiments, an electrohydrodynamic ("EHD") aerosol device is used to deliver the compounds disclosed herein and/or pharmaceutical compositions thereof. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, International Publication No. WO 94/12285; Coffee, International Publication No. WO 94/14543; Coffee, International Publication No. WO 95/26234; Coffee, International Publication No. WO 95/26235; Coffee, International Publication No. WO 95/32807). Other methods of intra-pulmonary delivery of a compound disclosed herein and/or pharmaceutical composition thereof are known to the skilled artisan and are within the scope of the present disclosure.

Transdermal devices can also be used to deliver the compounds disclosed herein and/or pharmaceutical compositions thereof. In some embodiments, the transdermal device is a matrix type transdermal device (Miller et al., International Publication No. WO 2004/041324). In other embodiments, the transdermal device is a multi-laminate transdermal device (Miller, United States Patent Application Publication No. 2005/0037059).

The amount of compounds disclosed herein and/or pharmaceutical compositions thereof that will be effective in the treatment or prevention of diseases in a patient will depend on the specific nature of the condition and can be determined by standard clinical techniques known in the art. The amount of compounds disclosed herein and/or pharmaceutical compositions thereof administered will, of course, be dependent on, among other factors, the subject being treated, the weight of the subject, the severity of the affliction, the manner of administration and the judgment of the prescribing physician.

4.7 Combination Therapy

In certain embodiments, compounds disclosed herein and/or pharmaceutical compositions thereof can be used in combination therapy with at least one other therapeutic agent. The compounds disclosed herein and/or pharmaceutical compositions thereof and the therapeutic agent can act additively or, more preferably, synergistically. In some embodiments, compounds disclosed herein and/or pharmaceutical compositions thereof are administered concurrently with the administration of another therapeutic agent. For example, compounds disclosed herein and/or pharmaceutical compositions thereof may be administered together with another therapeutic agent. In other embodiments, compounds disclosed herein and/or pharmaceutical compositions thereof are administered prior or subsequent to administration of other therapeutic agents.

5. EXAMPLES

Reference is now made to the following examples. It will be apparent to those skilled in the art that many modifications, both to materials and methods, may be practiced without departing from the scope of the disclosure.

5.1. Synthesis of Codeine Prodrug

Step A: Coupling of 4-amino benzyl alcohol with N,N'-diprotected lysine Derivative A

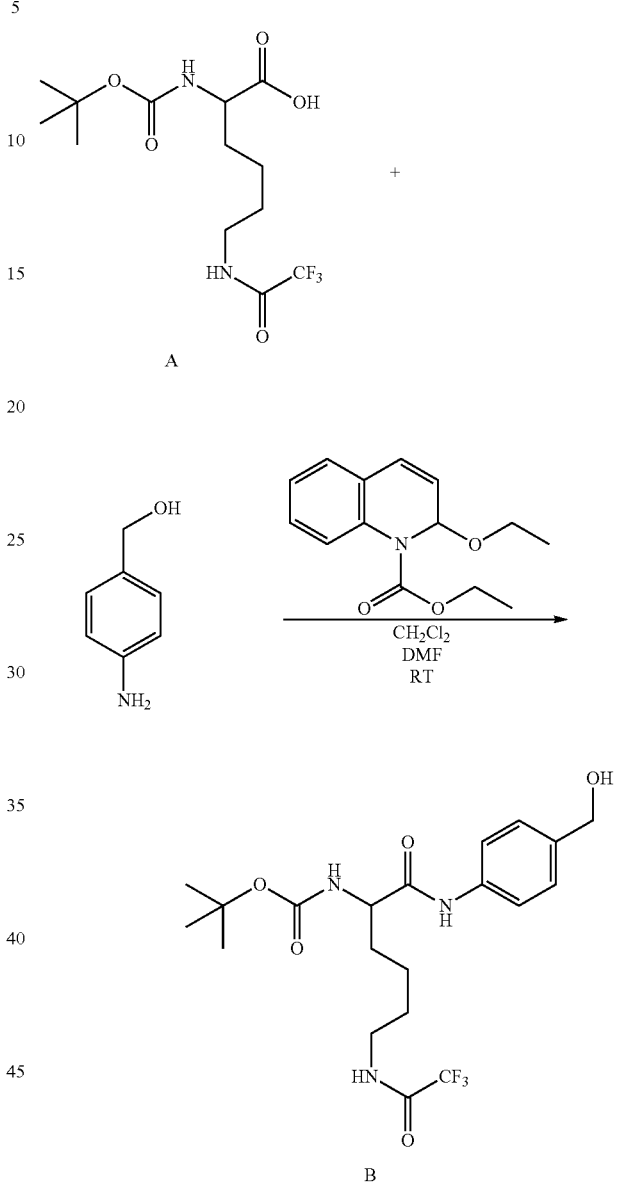

Amine (122 mg, 1 mmol) was added to a solution of acid A (342 mg, 1 mmol) in a mixture of methylene chloride (5 ml) and dimethylformamide (1 ml) followed by the addition of EEDQ (242.29 mg, 1 mmol). After 30 minutes of vigorous stirring a thick white solid formed which was dissolved by the addition of additional methylene chloride (5 ml) and dimethylformamide (1.5 ml). The reaction mixture was allowed to stir overnight at room temperature. The reaction was then diluted with ethyl acetate (5 ml) and transferred to a separatory funnel and washed with water (3×20 ml), brine (1×10 ml), dried over $Na_2SO_4$ then filtered and concentrated to yield 330 mgs of a crude oil which solidified upon standing. The crude solid was purified using flash chromatography employing ethyl acetate/hexane (1:1) as the eluting solvent to yield 130 mgs of desired amide B. The identity of B was confirmed by $^1H$ NMR analysis.

Step B: Conversion of N,N'-diprotected lysine (4-hydroxymethyl)anilide B to benzyl chloride C.

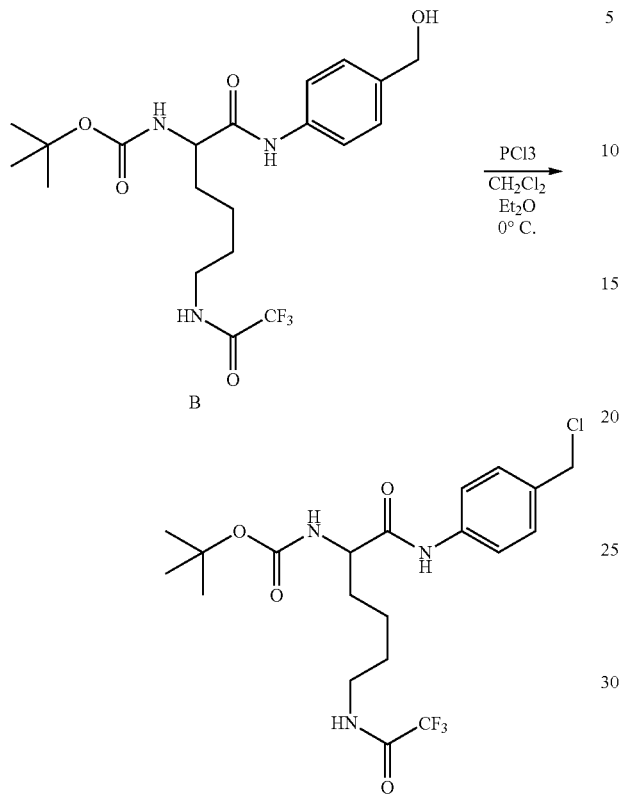

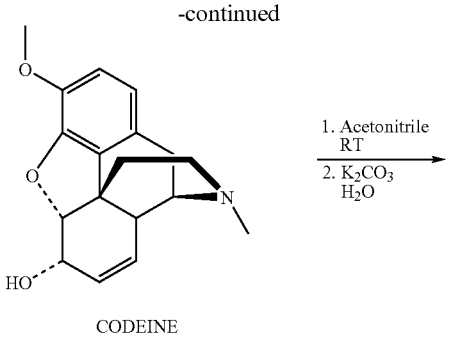

Benzyl alcohol B (1.34 g, 2.99 mmol) was suspended in a mixture of diethyl ether (10 ml) and methylene chloride (2.5 ml). The suspension was cooled to 0° C. and PCl₃ was added dropwise. The reaction was stirred for 1 h at 0° C. then poured into a saturated solution of NaHCO₃ and extracted with ethyl acetate (3×80 ml). The combined organic layers were dried over Na2SO4, filtered, and concentrated to yield 0.9 g of crude oil. The crude oil was purified via flash chromatography using ethyl acetate: hexane (1:1) as the eluting solvent to yield 670 mg of desired benzyl chloride analog C. The identity of compound C was confirmed by LC-MS analysis and used immediately in the subsequent step.

Step C: Alkylation of Codeine with Benzyl Chloride C to Yield D

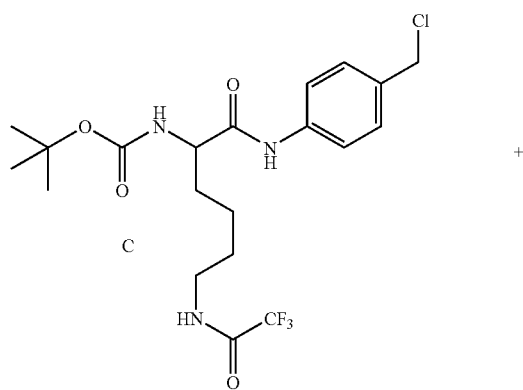

Codeine (290 mg, 0.97 mmol) was added to a solution of benzyl chloride C dissolved in acetonitrile (10 ml) at room temperature. The reaction was stirred for several days at room temperature then the solvent was removed under vacuum. The resulting residue was partitioned between ethyl acetate (20 ml) and water (20 ml). The aqueous layer was washed with ethyl acetate (20 ml) and concentrated under reduced pressure to yield 570 mgs of the desired TFA protected codeine quaternary salt (97% pure by HPLC analysis). 4.1 mg of this material was deprotected via exposure to an aqueous solution of K₂CO₃ (4.0 mg) in water (200 ul) for 18 hours to afford the desired product D. The identity of D was confirmed by LC-MS analysis.

5.2. Synthesis of Compound G Related to Structural Formula (VI)

Step A:

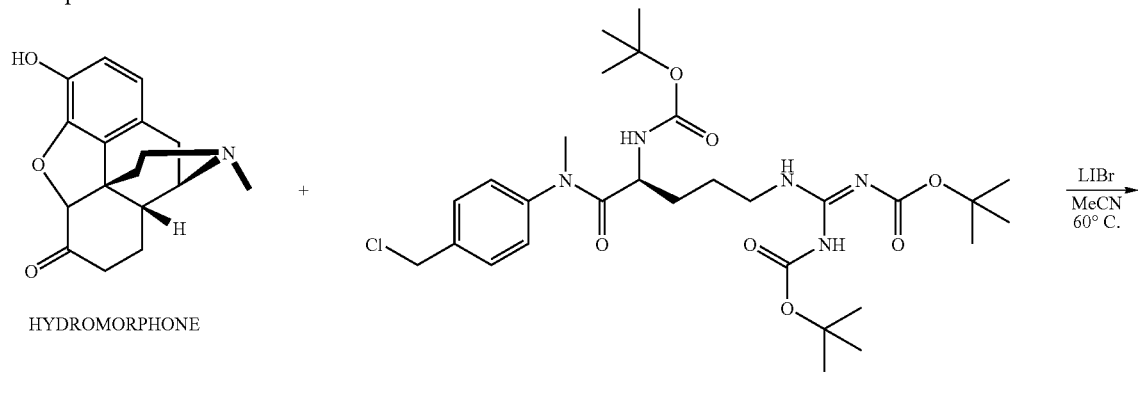

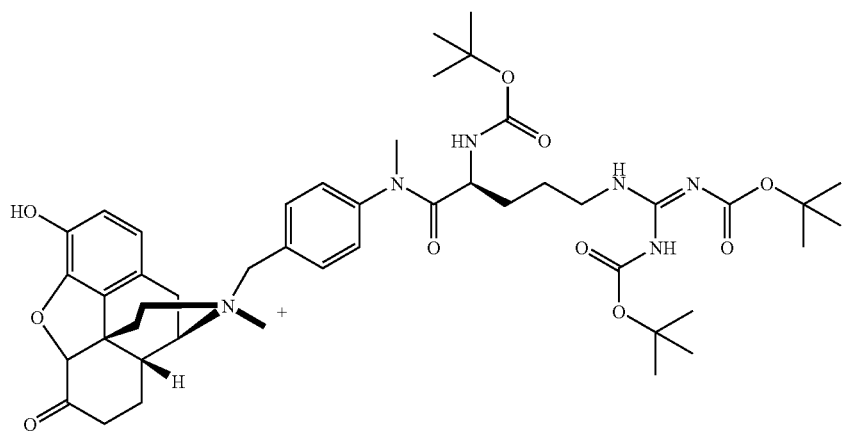

Hydromorphone E F

Hydromorphone (29 mg, 0.1 mmol) was added to a solution of (S)-N-(α,ω,ω)-tris(Boc)-2-amino-N-methyl-N-(4-(chloromethylphenyl)-5-guanidinopentanamide (68 mg, 0.11 mmol) and lithium bromide (9.0 mg, 0.1 mmol) in 1 ml of anhydrous acetonitrile. The mixture was stirred for 4 hours at 65° C. The mixture was cooled to room temperature; a precipitate was filtered out, washed with 1 ml of acetonitrile and dried on air, yielding 38 mg (40%) of the crude quaternary salt. MS: found 861.3, for $C_{46}H_{65}N_6O_{10}^+$ calculated 861.48.

Step B: Deprotection of Hydromorphone Benzyl Quaternary Salt F to Yield G

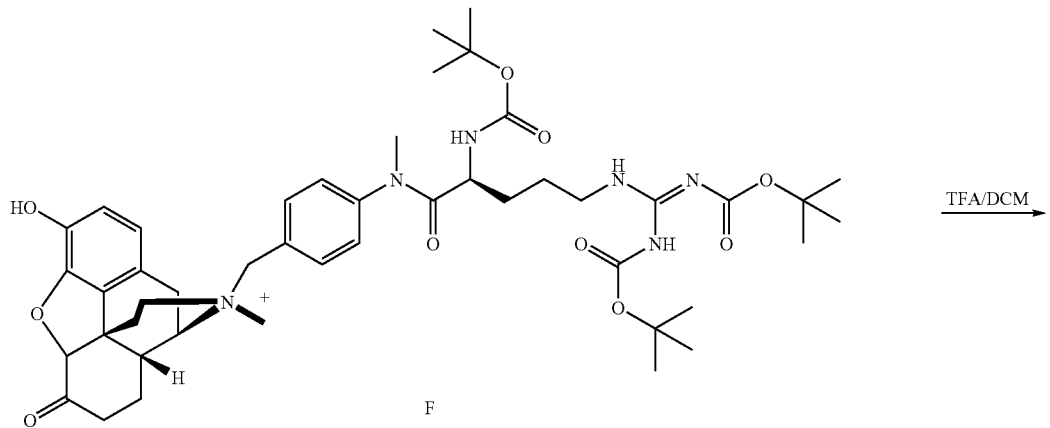

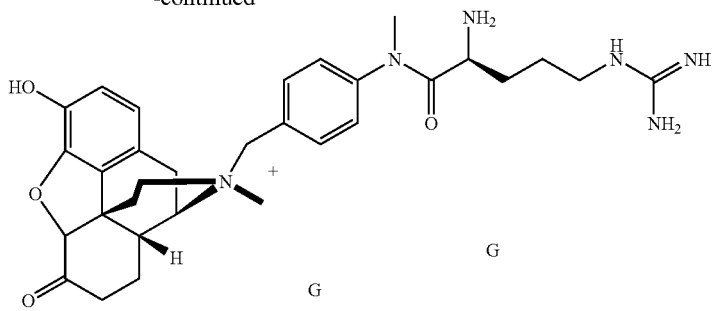

G

Tris(Boc)-derivative F (38 mg, 0.04 mmol) was dissolved in 4 ml of dichloromethane and 1 ml of trifluoroacetic acid was added dropwise to the above solution. The reaction mixture was stirred for 2 hours; the solvents were removed in vacuum and the product was purified by prep HPLC (acetonitrile gradient) yielding 10 mg (42%) of quaternary salt G. MS: found 561.2, for $C_{31}H_{41}N_6O_4^+$ calculated 561.32.

5.3. Trypsin Hydrolysis of Opioid Prodrug Z

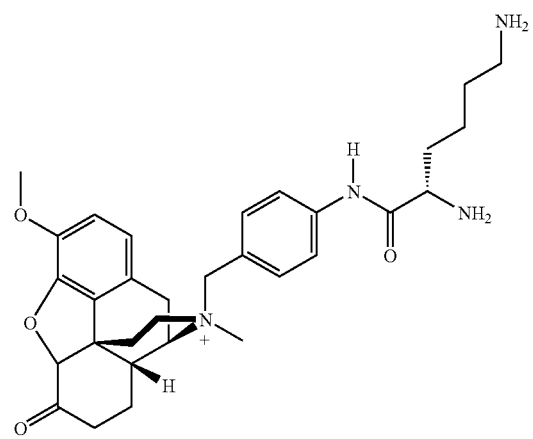

Opioid Prodrug Z

To 20 μL of the compound opioid prodrug Z (100 mM stock solution in DMSO) in 975 μL reaction buffer (12 mM $CaCl_2$, 5 mM Tris-HCl pH 8.0) is added 5 μL Type 1 bovine trypsin (1.0 mg/mL Type 1, bovine, Sigma Chemical Company). As the reaction proceeds 50 μL aliquots are removed at specific time points, quenched into 100 μL acetonitrile, and analyzed by HPLC for the disappearance of prodrug and/or the appearance of parent (hydrocodone). This concentration of trypsin (5 μL/mL of a 2.5 mg/mL stock solution) is set to 1×. Subsequent experiments that vary trypsin concentration are multiples of this concentration (e.g. 0.5×, 2×, 4×).

The opioid prodrug Z is hydrolyzed to hydrocodone as show in FIGS. 1A-B. FIG. 1A shows the % of compound opioid prodrug Z remaining after a 30 minute incubation at room temperature with increasing amounts of trypsin as measured by reverse phase HPLC. FIG. 1B shows the appearance of hydrocodone after a 30 minute incubation at room temperature with increasing amounts of trypsin as measured by reverse phase HPLC.

It will be apparent to those skilled in the art that many modifications, both to materials and methods, may be practiced without departing from the scope of this disclosure. Accordingly, the present embodiments are to be considered as illustrative and not restrictive, and the invention is not to be limited to the details given herein, but may be modified within the scope and equivalents of the allowed claims. All publications and patents cited herein are incorporated by reference in their entirety.

What is claimed is:

1. A compound of structural Formula:

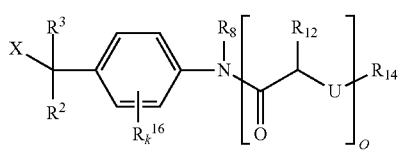

or salts thereof wherein:

X is an opioid, an amphetamine, or a phenidate and X is covalently bonded to —$(CR^2R^3)$—via an amine, a phenol, a carboxylic acid or a thiol;

$R^2$ and $R^3$ are independently hydrogen, alkyl, substituted alkyl, alkoxy, substituted alkoxy, aryl, substituted aryl, arylalkyl, substituted arylalkyl, heteroaryl, substituted heteroaryl, heteroarylalkyl or substituted heteroarylalkyl;

$R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —$OP(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ and —$C(NR^6)NR^5R^4$, and k is 0, 1, 2, 3, or 4;

$R^4$, $R^5$, $R^6$ and $R^7$ are independently hydrogen, alkyl, substituted alkyl, cycloalkyl, substituted cycloalkyl, cycloheteroalkyl, substituted cycloheteroalkyl, aryl, substituted aryl, heteroaryl or substituted heteroaryl, or optionally $R^4$ and $R^5$ together with the nitrogen atom to which they are bonded form a cycloheteroalkyl or substituted cycloheteroalkyl ring;

$R^8$ is hydrogen or methyl;

$R^{12}$ is an amino acid side chain;

each U is independently —$NR^{13}$—, —O— or —S—;

each $R^{13}$ is independently hydrogen, alkyl, substituted alkyl, aryl, substituted aryl, arylalkyl, substituted arylalkyl, heteroaryl, substituted heteroaryl, heteroarylalkyl or substituted heteroarylalkyl or optionally, $R^{13}$ and $R^{14}$ together with the atoms to which they are bonded form a cycloheteroalkyl or substituted cycloheteroalkyl ring; and $R^{14}$ is hydrogen, acyl, or —CO$_2$—t—butyl; and o is an integer from 1 to 5.

2. The compound of claim 1 in which X is an opioid.

3. The compound of claim 1 in which X is morphine, codeine, diacetylmorphine, hydrocodone, hydromorphone, levorphanol, oxycodone, oxymorphone, naltrexone, nalbuphine, butorphanol, nalorphine, alfentanil, buprenorphine, carfentanil, dihydrocodeine, dihydroetorphine, diprenorphine, etorphine, fentanyl, levomethadyl acetate hydrochloride, lofentanil, meperidine, methadone, morphine, naloxone, methyl naltrexone, beta-hydroxy 3-methylfentanyl, N-methylnaltrexone, normorphine, propoxyphene, remifentanil, sufentanil, tilidine, thebaine, nalbuphine, nalmefene, neopine, penomorphone or tramadol.

4. The compound of claim 1 in which X is morphine, codeine, diacetylmorphine, etorphine, hydrocodone, hydromorphone, levorphanol, oxycodone, oxymorphone, naltrexone, nalbuphine, butorphanol, or nalorphine.

5. The compound of claim 1 in which X is oxycodone, hydrocodone, oxymorphone, hydromorphone or codeine.

6. The compound of claim 1 of structural Formula (III):

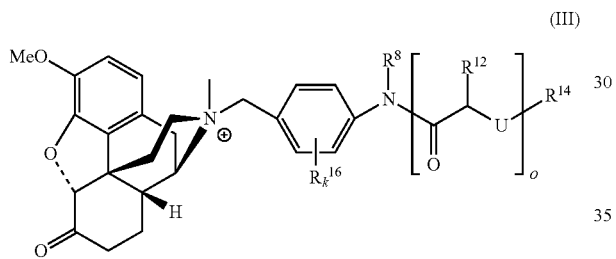

(III)

wherein $R^8$ is hydrogen or methyl, $R^{12}$ is an amino acid side chain, $R^{14}$ is hydrogen, acyl, or —CO$_2$-t-butyl, o is an integer from 1 to 5, $R_k^{16}$ are each independently selected from the group consisting of one or more of —F, —Cl, —Br, —I, —$R^4$, —O$^-$, —OR$^4$, —SR$^4$, —S$^-$, —NR$^4$R$^5$, —CF$_3$, —CN, —OCN, —SCN, —NO, —NO$_2$, —N$_3$, —S(O)$_2$O$^-$, —S(O)$_2$OH, —S(O)$_2$R$^4$, —OS(O$_2$)O$^-$, —OS(O)$_2$R$^4$, —P(O)(O$^-$)$_2$, —P(O)(OR$^4$)(O$^-$), —OP(O)(OR$^4$)(OR$^5$), —C(O)R$^4$, —C(S)R$^4$, —C(O)OR$^4$, —C(O)NR$^4$R$^5$, —C(O)O$^-$, —C(S)OR$^4$, —NR$^6$C(O)NR$^4$R$^5$, —NR$^6$C(S)NR$^4$R$^5$, —NR$^7$C(NR$^6$)NR$^5$R$^4$ and —C(NR$^6$)NR$^5$R$^4$, and k is 0, 1, 2, 3, or 4.

7. The compound of claim 1 of structural Formula (IV):

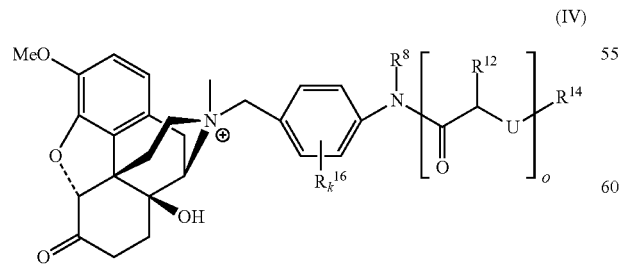

(IV)

wherein $R^8$ is hydrogen or methyl, $R^{12}$ is an amino acid side chain, $R^{14}$ is hydrogen, acyl, or —CO$_2$-t-butyl, o is an integer from 1 to 5, $R_k^{16}$ are each independently selected from the group consisting of one or more of —F, —Cl, —Br, —I, —$R^4$, —O$^-$, —OR$^4$, —SR$^4$, —S$^-$, —NR$^4$R$^5$, —CF$_3$, —CN, —OCN, —SCN, —NO, —NO$_2$, —N$_3$, —S(O)$_2$O$^-$, —S(O)$_2$OH, —S(O)$_2$R$^4$, —OS(O$_2$)O$^-$, —OS(O)$_2$R$^4$, —P(O)(O$^-$)$_2$, —P(O)(OR$^4$)(O$^-$), —OP(O)(OR$^4$)(OR$^5$), —C(O)R$^4$, —C(S)R$^4$, —C(O)OR$^4$, —C(O)NR$^4$R$^5$, —C(O)O$^-$, —C(S)OR$^4$, —NR$^6$C(O)NR$^4$R$^5$, —NR$^6$C(S)NR$^4$R$^5$, —NR$^7$C(NR$^6$)NR$^5$R$^4$ and —C(NR$^6$)NR$^5$R$^4$, and k is 0, 1, 2, 3, or 4.

8. The compound of claim 1 of structural Formula (V):

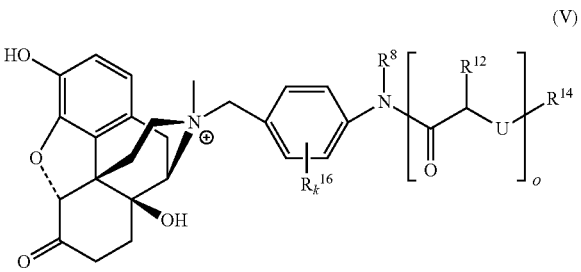

(V)

wherein $R^8$ is hydrogen or methyl, $R^{12}$ is an amino acid side chain, $R^{14}$ is hydrogen, acyl, or —CO$_2$-t-butyl, o is an integer from 1 to 5, $R_k^{16}$ are each independently selected from the group consisting of one or more of —F, —Cl, —Br, —I, —$R^4$, —O$^-$, —OR$^4$, —SR$^4$, —S$^-$, —NR$^4$R$^5$, —CF$_3$, —CN, —OCN, —SCN, —NO, —NO$_2$, —N$_3$, —S(O)$_2$O$^-$, —S(O)$_2$OH, —S(O)$_2$R$^4$, —OS(O$_2$)O$^-$, —OS(O)$_2$R$^4$, —P(O)(O$^-$)$_2$, —P(O)(OR$^4$)(O$^-$), —OP(O)(OR$^4$)(OR$^5$), —C(O)R$^4$, —C(S)R$^4$, —C(O)OR$^4$, —C(O)NR$^4$R$^5$, —C(O)O$^-$, —C(S)OR$^4$, —NR$^6$C(O)NR$^4$R$^5$, —NR$^6$C(S)NR$^4$R$^5$, —NR$^7$C(NR$^6$)NR$^5$R$^4$ and —C(NR$^6$)NR$^5$R$^4$, and k is 0, 1, 2, 3, or 4.

9. The compound of claim 1 of structural Formula (VI):

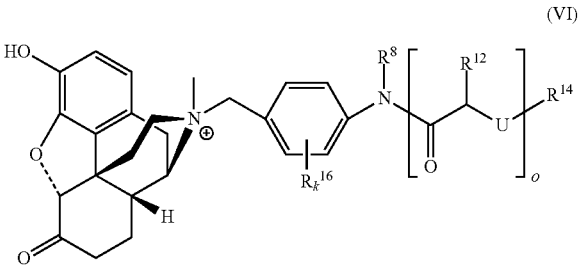

(VI)

wherein $R^8$ is hydrogen or methyl, $R^{12}$ is an amino acid side chain, $R^{14}$ is hydrogen, acyl, or —CO$_2$-t-butyl, o is an integer from 1 to 5, $R_k^{16}$ are each independently selected from the group consisting of one or more of —F, —Cl, —Br, —I, —$R^4$, —O$^-$, —OR$^4$, —SR$^4$, —S$^-$, —NR$^4$R$^5$, —CF$_3$, —CN, —OCN, —SCN, —NO, —NO$_2$, —N$_3$, —S(O)$_2$O$^-$, —S(O)$_2$OH, —S(O)$_2$R$^4$, —OS(O$_2$)O$^-$, —OS(O)$_2$R$^4$, —P(O)(O$^-$)$_2$, —P(O)(OR$^4$)(O$^-$), —OP(O)(OR$^4$)(OR$^5$), —C(O)R$^4$, —C(S)R$^4$, —C(O)OR$^4$, —C(O)NR$^4$R$^5$, —C(O)O$^-$, —C(S)OR$^4$, —NR$^6$C(O)NR$^4$R$^5$, —NR$^6$C(S)NR$^4$R$^5$, —NR$^7$C(NR$^6$)NR$^5$R$^4$ and —C(NR$^6$)NR$^5$R$^4$, and k is 0, 1, 2, 3, or 4.

10. The compound of claim 1 of structural Formula (VII):

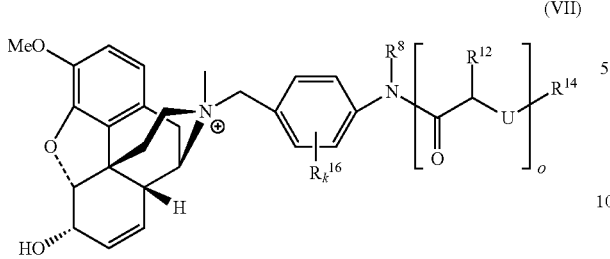

(VII)

wherein $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —OP$(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ and —$C(NR^6)NR^5R^4$, and k is 0, 1, 2, 3, or 4.

11. The compound of claim 1 of structural Formula (VIII):

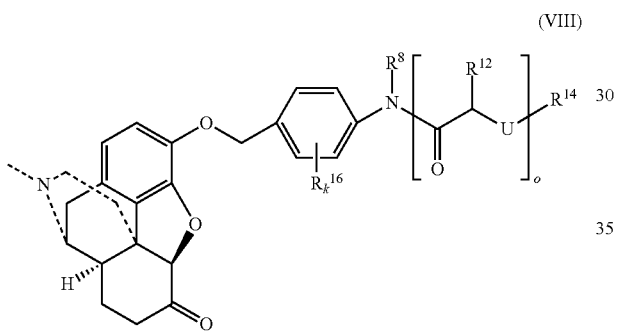

(VIII)

wherein $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —OP$(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ and —$C(NR^6)NR^5R^4$, and k is 0, 1, 2, 3, or 4.

12. The compound of claim 1 of structural Formula (IX):

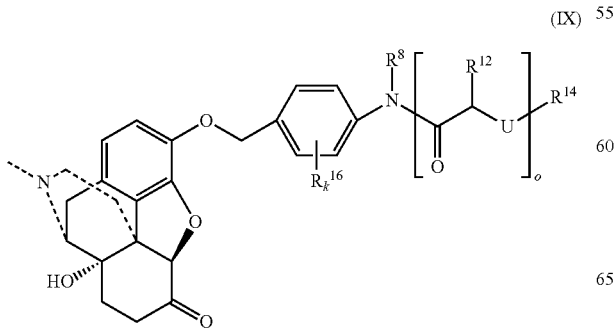

(IX)

wherein $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —OP$(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ and —$C(NR^6)NR^5R^4$, and k is 0, 1, 2, 3, or 4.

13. The compound of claim 1 of structural Formula (X):

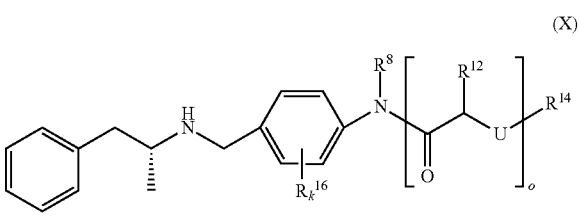

(X)

wherein $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —OP$(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ and —$C(NR^6)NR^5R^4$, and k is 0, 1, 2, 3, or 4.

14. The compound of claim 1 of structural Formula (XI):

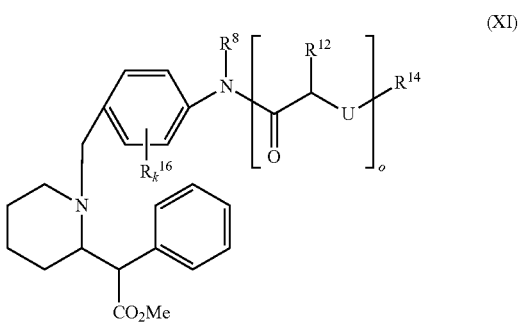

(XI)

wherein $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —OP$(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ and —$C(NR^6)NR^5R^4$, and k is 0, 1, 2, 3, or 4.

15. The compound of claim 1 of structural Formula (XII):

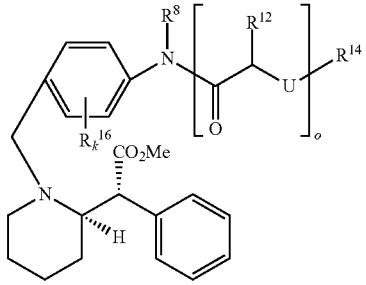

(XII)

wherein $R^8$ is hydrogen or methyl, $R^{12}$ is an amino acid side chain, $R^{14}$ is hydrogen, acyl, or —CO$_2$-t-butyl, o is an integer from 1 to 5, $R_k^{16}$ are each independently selected from the group consisting of one or more of —F, —Cl, —Br, —I, —R$^4$, —O$^-$, —OR$^4$, —SR$^4$, —S$^-$, —NR$^4$R$^5$, —CF$_3$, —CN, —OCN, —SCN, —NO, —NO$_2$, —N$_3$, —S(O)$_2$O$^-$, —S(O)$_2$OH, —S(O)$_2$R$^4$, —OS(O$_2$)O$^-$, —OS(O)$_2$R$^4$, —P(O)(O$^-$)$_2$, —P(O)(OR$^4$)(O$^-$), —OP(O)(OR$^4$)(OR$^5$), —C(O)R$^4$, —C(S)R$^4$, —C(O)OR$^4$, —C(O)NR$^4$R$^5$, —C(O)O$^-$, —C(S)OR$^4$, —NR$^6$C(O)NR$^4$R$^5$, —NR$^6$C(S)NR$^4$R$^5$, —NR$^7$C(NR$^6$)NR$^5$R$^4$ and —C(NR$^6$)NR$^5$R$^4$, and k is 0, 1, 2, 3, or 4.

16. The compound of claim 1 in which X is an amphetamine or a methyphenidate.

17. The compound of claim 1 in which X is selected from the group consisting of amphetamine, dextroamphetamine, methamphetamine, p-methoxy amphetamine, methylenedioxyamphetamine, 2,5-dimethoxy-4-methylamphetamine, 2,4,5-trimethoxyamphetamine, 3,4-methylenedioxyamphetamine, methylphenidate, and D-methylphenidate.

18. The compound of claim 1 in which X is an opioid;
$R^2$ and $R^3$ are independently hydrogen, alkyl, aryl or arylalkyl; and
$R^{12}$ is methyl, benzyl, —CH$_2$CO$_2$H, —CH$_2$(CH$_2$)$_3$NH$_2$ or —CH$_2$CH$_2$CH$_2$NHC(NH)NH$_2$ and
$R^{13}$ is hydrogen.

19. The compound of claim 18 in which o is 2, the $R^{12}$ closest to the opioid is —CH$_2$(CH$_2$)$_3$NH$_2$ or —CH$_2$CH$_2$CH$_2$NHC(NH)NH$_2$, any other $R^{12}$ is hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, homobenzyl, 4-hydroxybenzyl, 4-bromobenzyl, 4-imidazolylmethyl or 3indolylmethyl, U is NR$^{13}$ and each $R^{13}$ is hydrogen.

20. A method of reducing or deterring abuse of a drug, comprising providing to a patient a therapeutically effective amount of the compound of claim 1.

21. The compound of claim 1 of structural Formula:

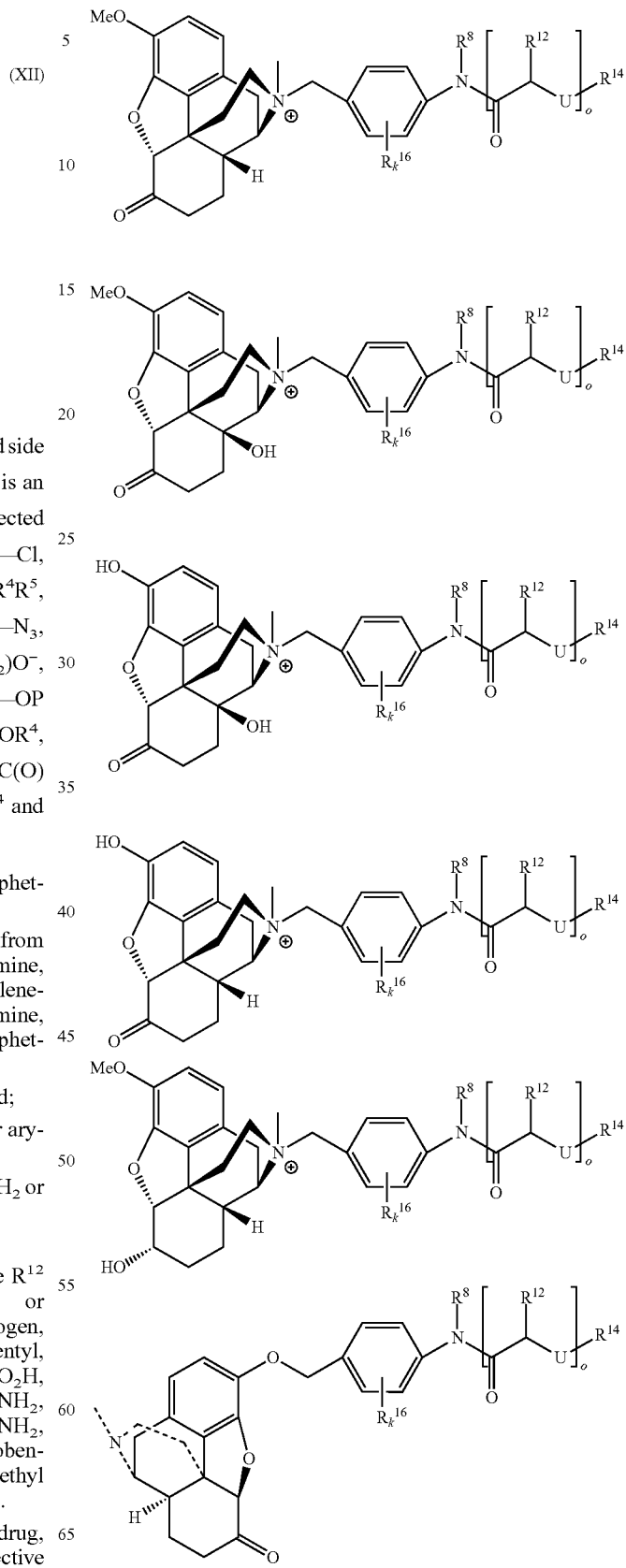

-continued

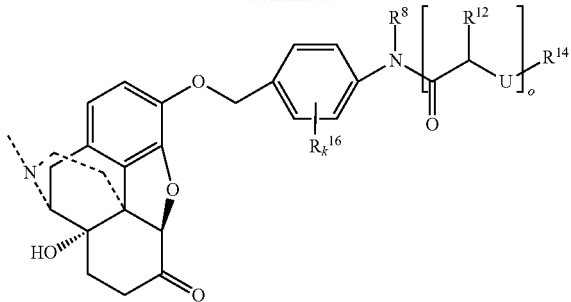

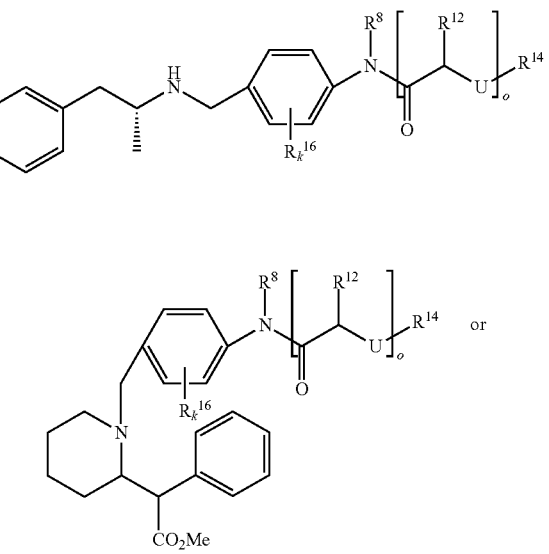

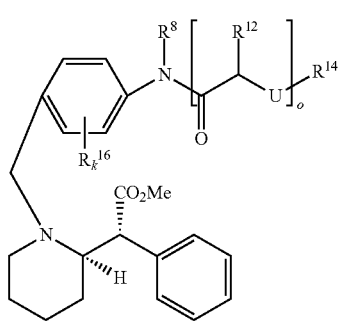

wherein $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —OP(O)($OR^4$)($OR^5$), —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ and —$C(NR^6)NR^5R^4$, and k is 0, 1, 2, 3, or 4.

22. The compound of claim 1 of structural Formula:

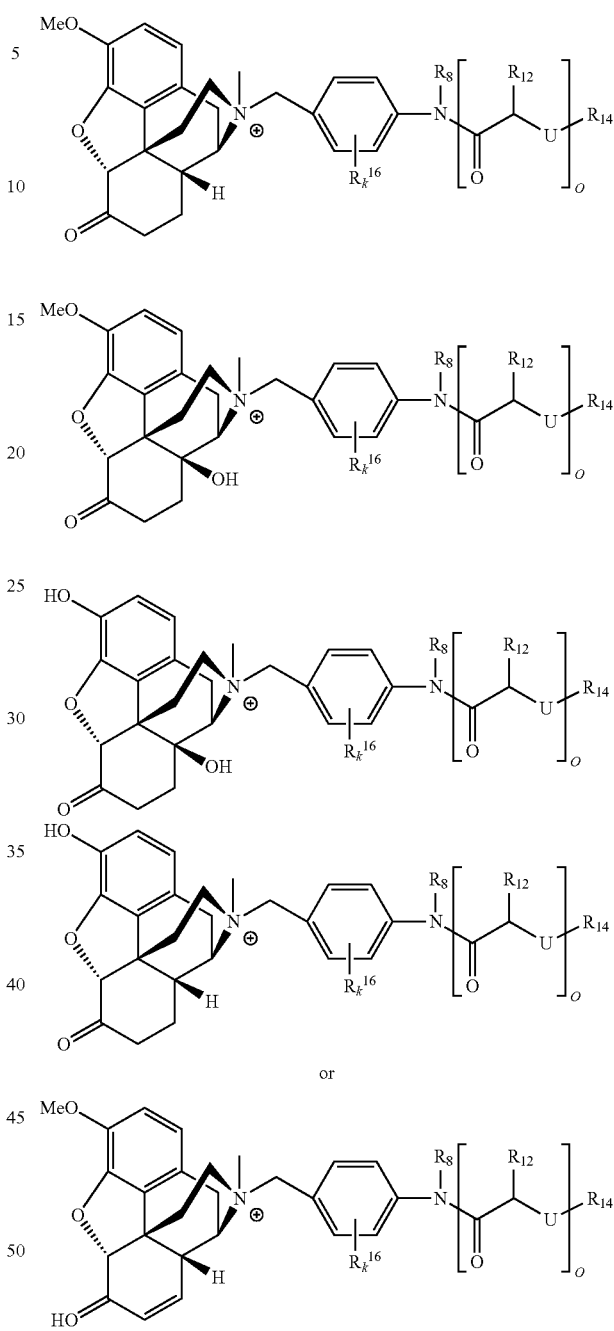

wherein $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —OP(O)($OR^4$)($OR^5$), —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ and —$C(NR^6)NR^5R^4$, and k is 0, 1, 2, 3, or 4.

23. The compound of claim 1 of structural Formula:

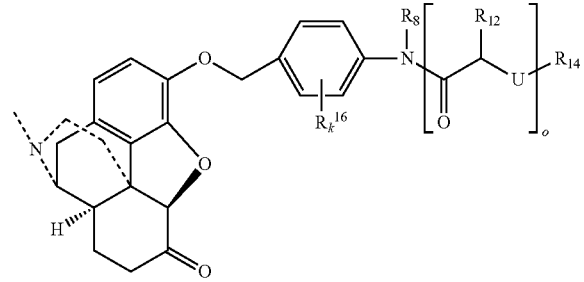

or

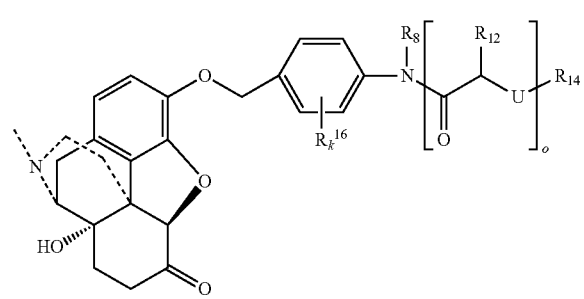

wherein $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —OP$(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ and —$C(NR^6)NR^5R^4$, and k is 0, 1, 2, 3, or 4.

24. The compound of claim 1 of structural Formula:

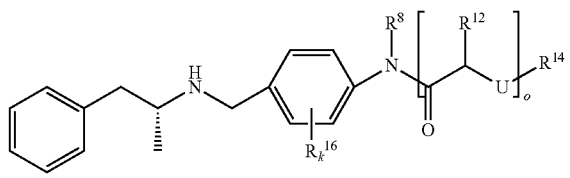

-continued

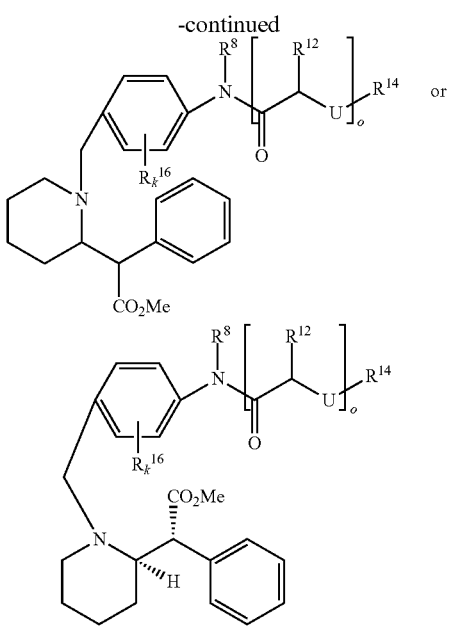

wherein $R^8$ is hydrogen or methyl, $R^{12}$ is an amino acid side chain, $R^{14}$ is hydrogen, acyl, or —$CO_2$-t-butyl, o is an integer from 1 to 5, $R_k^{16}$ are each independently selected from the group consisting of one or more of —F, —Cl, —Br, —I, —$R^4$, —$O^-$, —$OR^4$, —$SR^4$, —$S^-$, —$NR^4R^5$, —$CF_3$, —CN, —OCN, —SCN, —NO, —$NO_2$, —$N_3$, —$S(O)_2O^-$, —$S(O)_2OH$, —$S(O)_2R^4$, —$OS(O_2)O^-$, —$OS(O)_2R^4$, —$P(O)(O^-)_2$, —$P(O)(OR^4)(O^-)$, —OP$(O)(OR^4)(OR^5)$, —$C(O)R^4$, —$C(S)R^4$, —$C(O)OR^4$, —$C(O)NR^4R^5$, —$C(O)O^-$, —$C(S)OR^4$, —$NR^6C(O)NR^4R^5$, —$NR^6C(S)NR^4R^5$, —$NR^7C(NR^6)NR^5R^4$ and —$C(NR^6)NR^5R^4$, and k is 0, 1, 2, 3, or 4.

25. A method of treating attention deficit hyperactivity disorder (ADHD), depression, obesity or narcolepsy in a patient comprising administering to a patient in need of such treatment a therapeutically effective amount of the compound of claim 1 wherein X is an amphetamine or a methylphenidate.

26. A pharmaceutical composition comprising the compound of claim 1 and a pharmaceutically acceptable vehicle.

27. A method of treating pain in a patient comprising administering to a patient in need of such treatment a therapeutically effective amount of the compound of claim 1, wherein X is an opioid.

28. The method of claim 27 in which the pain is acute pain, chronic pain, neuropathic pain, arthritic pain, osteoarthritic pain, rheumatoid arthritic pain, musculoskeletal pain, myofascial pain, cancer pain, visceral pain, diabetic pain, muscular pain, post-herpetic neuralgic pain, chronic pelvic pain, endometriosis pain or pelvic inflammatory pain.

* * * * *